United States Patent
Bodepudi et al.

(10) Patent No.: US 7,947,817 B2
(45) Date of Patent: *May 24, 2011

(54) SYNTHESIS AND COMPOSITIONS OF 2'-TERMINATOR NUCLEOTIDES

(75) Inventors: Veeraiah Bodepudi, San Ramon, CA (US); Stephen Gordon Will, Oakland, CA (US); David Harrow Gelfand, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1041 days.

This patent is subject to a terminal disclaimer.

(21) Appl. No.: 10/879,494

(22) Filed: Jun. 28, 2004

(65) Prior Publication Data

US 2005/0037991 A1    Feb. 17, 2005

Related U.S. Application Data

(60) Provisional application No. 60/483,861, filed on Jun. 30, 2003, provisional application No. 60/519,661, filed on Nov. 12, 2003.

(51) Int. Cl.
C07H 19/00 (2006.01)
C07H 21/00 (2006.01)
C12Q 1/68 (2006.01)

(52) U.S. Cl. .................. 536/22.1; 536/25.3; 435/6
(58) Field of Classification Search .............. 536/22.1, 536/25.3; 435/6
See application file for complete search history.

(56) References Cited

U.S. PATENT DOCUMENTS

| | | | |
|---|---|---|---|
| 3,338,882 A | 8/1967 | Wechter | |
| 4,469,863 A | 9/1984 | Ts'o et al. | |
| 4,889,818 A | 12/1989 | Gelfand et al. | |
| 5,034,506 A | 7/1991 | Summerton et al. | |
| 5,216,141 A | 6/1993 | Benner | |
| 5,235,033 A | 8/1993 | Summerton et al. | |
| 5,374,553 A | 12/1994 | Gelfend et al. | |
| 5,386,023 A | 1/1995 | Sanghvi et al. | |
| 5,420,029 A | 5/1995 | Gelfend et al. | |
| 5,455,170 A | 10/1995 | Abramson et al. | |
| 5,466,591 A | 11/1995 | Abramson et al. | |
| 5,466,786 A * | 11/1995 | Buhr et al. | 536/26.26 |
| 5,532,130 A | 7/1996 | Alul | |
| 5,547,835 A | 8/1996 | Köster | |
| 5,602,240 A | 2/1997 | De Mesmaeker et al. | |
| 5,618,711 A | 4/1997 | Gelfand et al. | |
| 5,624,833 A | 4/1997 | Gelfand et al. | |
| 5,637,684 A | 6/1997 | Cook et al. | |
| 5,644,048 A | 7/1997 | Yau | |
| 5,674,738 A | 10/1997 | Abramson et al. | |
| 5,750,673 A | 5/1998 | Martin | |
| 5,789,224 A | 8/1998 | Gelfend et al. | |
| 5,795,762 A | 8/1998 | Abramson et al. | |
| 5,914,396 A | 6/1999 | Cook et al. | |
| 5,939,292 A | 8/1999 | Gelfend et al. | |
| 5,990,303 A | 11/1999 | Seela | |
| 6,147,200 A | 11/2000 | Manoharan et al. | |
| 6,184,364 B1 | 2/2001 | Picken et al. | |
| 6,495,671 B1 | 12/2002 | Manoharan et al. | |
| 6,531,584 B1 * | 3/2003 | Cook et al. | 536/23.1 |
| 6,921,812 B1 | 7/2005 | Prakash et al. | |
| 2001/0041794 A1 | 11/2001 | Bischofberger et al. | |
| 2002/0012970 A1 | 1/2002 | Smith et al. | |
| 2004/0005599 A1 | 1/2004 | Schoenbrunner et al. | |
| 2004/0023240 A1 | 2/2004 | Marliere et al. | |
| 2007/0154914 A1 | 7/2007 | Gelfand et al. | |

FOREIGN PATENT DOCUMENTS

| | | |
|---|---|---|
| CH | 518 950 | 2/1972 |
| DE | 3803021 A1 | 8/1989 |
| EP | 0 063 879 A2 | 4/1982 |
| EP | 0252683 B1 | 1/1995 |
| EP | 2007008997 | 10/2007 |
| JP | 52090693 | 2/1977 |
| JP | 03178985 | 8/1991 |
| JP | 3178985 A | 8/1991 |
| JP | 09316093 | 12/1997 |
| WO | 9416101 A2 | 7/1994 |
| WO | 9416101 A3 | 7/1994 |
| WO | WO 01/90121 A2 | 11/2001 |
| WO | WO 01/96354 A1 | 12/2001 |
| WO | WO 02/057425 A2 | 7/2002 |
| WO | WO 03/004603 A2 | 1/2003 |
| WO | 2005005667 A2 | 1/2005 |
| WO | 2005005667 A3 | 1/2005 |
| WO | WO 2005/005667 A2 | 1/2005 |
| WO | 2005118608 A2 | 12/2005 |
| WO | 2005118608 A3 | 12/2005 |
| WO | 2007075967 A2 | 7/2007 |
| WO | 2007075967 A3 | 7/2007 |
| WO | WO 2004/021075 | 7/2007 |

OTHER PUBLICATIONS

Hamel, 1976, Derivatives of Guanosine Triphosphate with Ribose 2'-Hydroxyl Substituents, Eur. J. Biochem., 70: 339-347.*
Hamel et al., 1981, Interaction of tubulin with ribose-modified analogs of GTP and GDP: Evidence for two mutually exclusive exchangeable nucleotide binding sites, PNAS, 78(6): 3368-3372.*
Hayakawa et al., 1998, Bioorganic & Medicinal Chemistry Letter, 8: 2559-2562.*
Azuma et al., 2001, Mol. Pharmacol., 59: 725-731.*
Zhang, Jia, et al., 2005 "Proofreading genotyping assays mediated by high fidelity exo + DNA polymerases", Trends in Biotechnology, 23(2):92-96.
Messens, E., et al. (1968) "The Synthesis of Nucleoside 2' (3')—Phosphate 5'—Triphosphates," *FEBS Letters*, vol. 1, No. 5: 326-328.
U.S. Appl. No. 60/483,861, filed Jun. 30, 2003, Gelfand et al.
Adams et al. (1969) "Nucleotide sequence from the coat protein cistron of R17 bacteriophage RNA." *Nature* 223(210): 1009-1014.
Beaucage and Iyer (1993) "The Functionalization of Oligonucleotides via Phosphoramidite Derivative." *Tetrahedron* 49(10): 1925-1963.
Brill et al. (1989) "Synthesis of Oligodeoxynucleoside Phosphorodithioates via Thioamid." *Journal of American Chemistry Society* 111:2321-2323.

(Continued)

*Primary Examiner* — Amber D. Steele
(74) *Attorney, Agent, or Firm* — Olga Kay; Rhea Nersesian

(57) ABSTRACT

The invention provides compositions that comprise nucleotides and/or nucleosides having blocking groups at 2'-positions of sugar moieties. Methods of synthesizing these nucleic acids are also provided.

25 Claims, 24 Drawing Sheets

OTHER PUBLICATIONS

Brownlee et al. (1967) "Molecular Structure: Nucleotide Sequence of 5S-ribosomal RNA from *Escherichia coli.*" *Nature* 215(102): 735-736.

Carlsson et al. (1996) 'Screening for Genetic Mutations. *Nature* 380:207.

Carroll et al. (2003) "Inhibition of Hepatitis C Virus RNA Replication by 2'-Modified Nucleoside Analogs." *The Journal of Biological Chemistry* 278(14): 11979-11984.

Denpcy et al. (1995) "Synthesis of a Thymidyl Pentamer of Deoxyribonucleic Guanidine and Binding Studies with DNA Homopolynucleotides." *Proceedings of the National Academy of Sciiences USA* 92: 6097-6101.

Egholm et al. (1992) "Peptide nucleic acids (PNA). Oligonucleotide analogs with an achiral peptide backbone." *al of American Chemistry Society* 114:1895-1897.

Egholm et al. (1993) "PNA hybridizes to complementary oligonucleotides obeying the Watson-Crick hydrogen-bonding rules." *Nature* 365:566-568.

Gao and Jeffs (1994) "Unusual conformation of a 3'-thioformacetal linkage in a DNA duplex." *Journal of Biomolecular NMR* 4:17-34.

Gilbert and Maxam (1973) The nucleotide sequence of the lac operator *Proceedings of the National Academy of Sciences USA* 70(12): 3581-3584.

Grein et al. (1994) "3-Deaza- and 7-Deazapurines: Duplex Stability of Oligonucleotides Containing Modified Adenine or Guanine Bases." *Bioorganic Medicinal Chemistry Letters* 4(8): 971-976.

Horn et al. (1996) "Oligonucleotides with alternating anionic and cationic phosphoramidate linkages: Synthesis and hybridization of stereo-uniform isomers." *Tetrahedron Letters* 37:743-764.

Jenkins and Turner (1995) "The Biosynthesis of Carbocyclic." *Chemical Society Review* 169-176.

Jung et al. (1994) "Hybridization of Alternating Cationic.Anionic Oligonucleotieds to RNA Segments." *Nucleoside & Nucleotide* 13 (6&7):1597-1605.

Kiedrowski et al. (1991) "Parabolic Growth of a Self-Replicating Hexadeoxynucleotide Bearing a 3'-5'-Phosphamidate Linkage." *Angew. Chem. Int. Ed. English* 30: 423-426.

Lee et al. (1992) "DNA sequencing with dye-labeled terminators and T7 DNA polymerase: effect of dyes and dNTPs on incorporation of dye-terminators and probability analysis of termination fragments,"*Nucleic Acid Res.* 20:2471.

Letsinger (1970) "Phosphoramidate Analogs of Oligonucleotides." *Journal of Organic Chemistry* 35(11): 3800-3803.

Letsinger et al. (1986) "Effects of pendant groups at phosphorus on binding properties of d-ApA analogues." *Nucleic Acids Research* 14: 3487-3499.

Letsinger et al. (1988) "Cationic oligonucleotides."*Journal of American Chemistry Society* 10:4470-4471.

Mag et al. (1991) "Synthesis and selective cleavage of an oligodeoxynucleotide containing a bridged internucleotide 5'-phosphorothioate linkage."*Nucleic Acids Research* 19(7):1437-1441.

Maxam and Gilbert (1977) A new method for sequencing DNA *Proceedings of the National Academy of Sciences USA* 74:560-564.

Meier and Engles (1992) "Peptide Nucleic Acids (PNAs)—Unusual Properties of Nonionic Oligonucleotide Analogues." *Angew. Chem. Int. Ed. English* 31(8):1008-1010.

Mesmaeker et al. (1994) "Comparison of Rigid and Flexible Backbones in Antisense Oligonucleotides." *Bioorganic & Medicinal Chemistry Letters* 4(3): 395-398.

Pauwels et al. (1986) "Biological Activity of New 2-5A Analogues." *Chemica Scripta* 26:141-145.

Sanger et al. (1973) "Use of DNA polymerase I primed by a synthetic oligonucleotide to determine a nucleotide sequence in phage fl DNA," *Proceedings of the National Academy of Sciences USA* 70(4): 1209-1213.

Sanger et al. (1977) "DNA sequencing with chain-terminating inhibitors," *Proceedings of the National Academy of Sciences USA* (74)12: 5463-5467.

Sanger et al. (1992) "DNA sequencing with chain-terminating inhibitors," *Milestones in Biotechnology* pp. 104-108.

Sanghvi and Cook (1994) ASC Symposium Series 580, "Carbohydrate Modifications in Antisense Research", Ed. Chapters 2 and 3.

Sauer et al. (2002) "Facile method for automated genotyping of single nucleotide polymorphisms by mass spectrometry," *Nucleic Acids Research* 30(5):e22.

Sawai (1984) "Synthesis and Properties of Oligoadenylic Acids Containing 2'-5' Phosphoramide Linkage." *Chemistry Letters*, pp. 805-808.

Seela and Becher (1999) "Oligonucleotides Containing Pyrazolo[3,4-d] pyrimidines: The Influence of 7-Substituted 8-Aza-7-deaza-2'-deoxyguanosines on the Duplex Structure and Stability." *Helvetica Chimic Acta* 82:1640-1655.

Seela and Lampe (1991) "3-Deazaguanine $N^7$—and $N^9$—(2'-Deoxy-$\beta$ -D-ribofuranosides): Building Blocks for Solid-Phase Synthesis and Inforporation into Oligodeoxyribonucleotides." *Helvetica Chimic Acta* 74:1790-1800.

Smith et al. (1986) "Fluorescence detection in automated DNA sequence analysis," *Nature* 321:674-679.

Sprinzl et al. (1977) "Enzymatic Incorporation of ATP and CTP Analogues into the 3' End of tRNA." *European Journal of Biochemistry* 81:579-589.

Bennett, G., et al, 1976, "Guanosine Tetraphosphate and Its Analogues. Chemical Synthesis of Guanonine 3',5'-Dipyrophosphate, Deoxyguanosine 3',5'-Dipyrophosphate, Guanosine 2', 5'-Bis (methylenediphosphonate), and Guanosine 3',5'-Bis(methylenediphosphonate)†", *Biochemistry*, 15 (21): 4623-4628.

Brill, W., et al, 1989, "Synthesis of Oligodeoxynucleoside Phosphorodithioates via Thioamidites", *J. Am. Chem. Soc.* 111: 2321-2322.

Burgess, K., et al, 2000, "Syntheses of Nucleoside Triphosphates", *Chem. Rev.* 100: 2047-2059.

Carroll, S., et al, 2000, "Only a Small Fraction of Purified Hepatitis C RNA-Dependent RNA Polymerase Is Catalytically Competent: Implications for Viral Replication and in Vitro Assays", *Biochemistry*, 39 :8243-8249.

Cheng, C., et al, 2001, "Phosphorylation of Adenosine with Trimetaphosphate Under Simulated Prebiotic Conditions", *Origins of Life and Evolution of the Biosphere*.

Crimmins, M., et al, 2000, "Solid-Phase Synthesis of Carbocyclic Nucleosides", *American Chemical Society*, 2 (8): 1065-1067.

Daluge, S., et al, 1997, "1592U89, a Novel Carbocyclic Nucleoside Analog with Potent, Selective Anti-Human Immunodeficiency Virus Activity", *Antimicrobial Agents and Chemotherapy*, 41 (5):1082-1093.

Etaix, E., et al, 1978, "Phosphorylation of Nucleosides in Aqueous Solution Using Trimetaphosphate: Formation of Nucleoside Triphosphates", *J. Carbohydrates • Nucleosides • Nucleotides*, 5 (2): 91-110.

Franchetti, P., et al, 1998, "2'-C-Methyl Analogues of Selective Adenosine Receptor Agonists: Synthesis and Binding Studies", *J. Med. Chem.*, 41: 1708-1715.

Hamel, E., 1976, "Derivatives of Guanosine Triphosphate with Ribose 2'-Hydroxyl Substituents", *Eur. J. Biochem.*, 70: 339-347.

Kleiber, J., et al, 2000, "Performance Characteristics of a Quantitative, Homogeneous TaqMan RT-PCR Test for HCV RNA", *Journal of Molecular Diagnostics*, 2 (3): 158-166.

Letsinger, R., et al, 1970, "Phosphoramidate Analogs of Oligonucleotides", *J. Org. Chem.*, 35 (11): 3800-3803.

Meng, Q., et al, 2001, "Automated Multiplex Assay System for Simultaneous Detection of Hepatitis B Virus DNA, Hepatitis C Virus RNA, and Human Immunodeficiency Virus Type 1 RNA", *Journal of Clinical Microbiology*, 39 (8): 2937-2945.

Mohanty, B., et al, 2000, "Polynucleotide phosphorylase functions both as a 3' → 5" exonuclease and a poly (A) polymerase in Escherichia coli", *PNAS*, 97 (22): 11966-11971.

Saffhill, R., et al, 1967, "Selective Phosphorylation of the cis-2',3'-Diol of Unprotected Ribonucleosides with Trimetaphosphate in Aqueous Solution", *J. Org. Chem.*, 35 (9): 2881-2883.

Sanger, F., et al, 1977, "DNA Sequencing with Chain-termination Inhibitors", *Proc. Natl. Acad. Sci. USA*, 74: 5463-5467.

Von Kiedrowski, G., et al, 1991, "Parabolic Growth of a Self-Replicating Hexadeoxynucleotide Bearing a 3'-5'-Phosphoamidate Linkage", *Angew. Chem. Int. Ed. Engl.*, 30 (4): 423-426.

Yamagata, Y., et al, 1995, "Spcific Effect of Magnesium ion on 2',3'-Cyclic amp Synthesis from Adenosine and Trimeta Phosphate in Aqueous Solution", Origins of Life and Evolution of the Biosphere, 25: 47-52.

Cashel, M., et al., 1976, "Interactions of ppGpp Structural Analogs with RNA Polymerase", Alfred Benzon Symposium, 9:279-291.

Cheng, Changmei, et al., 2002, "Phosphorylation of Adensoine with Trimetaphosphate Under Simulated Prebiotic Conditions", Origins of Life and Evolution of the Biosphere, 32:219-224.

Lee, Linda G., et al., 1992, "DNA Sequencing with dye-labeled terminators and T7 DNA polymerase: effect of dyes and dNTPs on incorporation of dye-terminators and probability analysis of termination fragments", Nucleic Acids Research, 20(10):2471-2483.

Lustbader, Jay, et al., 1982, "Di- and Triphosphate Derivatives of Acyclo- and Arabinosylguanne Effects on the Polymerization of Purified Tubulin", Biochimica et Biophysica Acta, 719:215-222.

Rosenblum, B. B., et al. 1997, "New Dye-Labeled Terminators for Improved DNA Sequencing Patterns", Nucleic Acids Research, 25(22):4500-4504.

Staffhill, R. 1970, "Selective Phosphorylation of the cis-2',3'-Diol of Unprotected Ribonucleosides with Trimetaphosphate in Aqueous Solution".

* cited by examiner

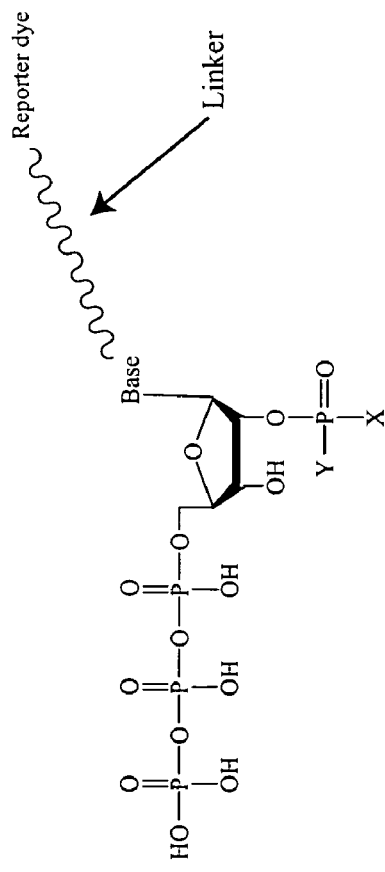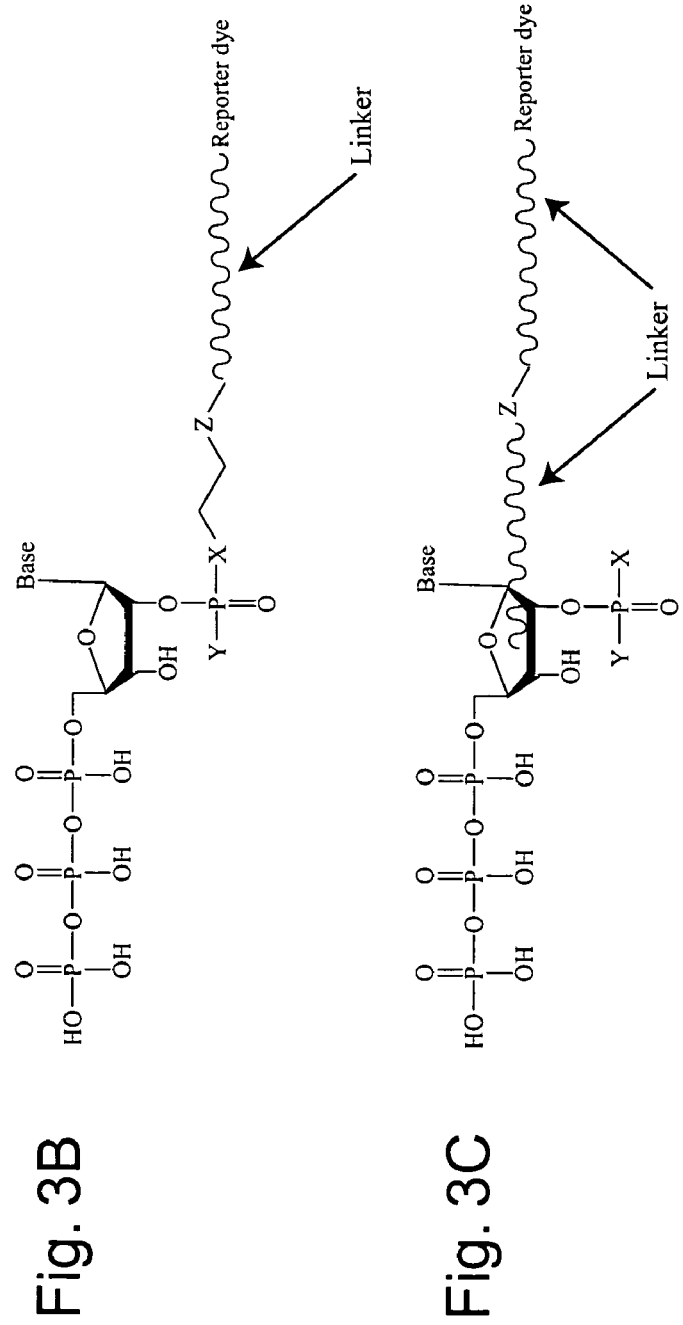
Fig. 3A
Fig. 3B
Fig. 3C

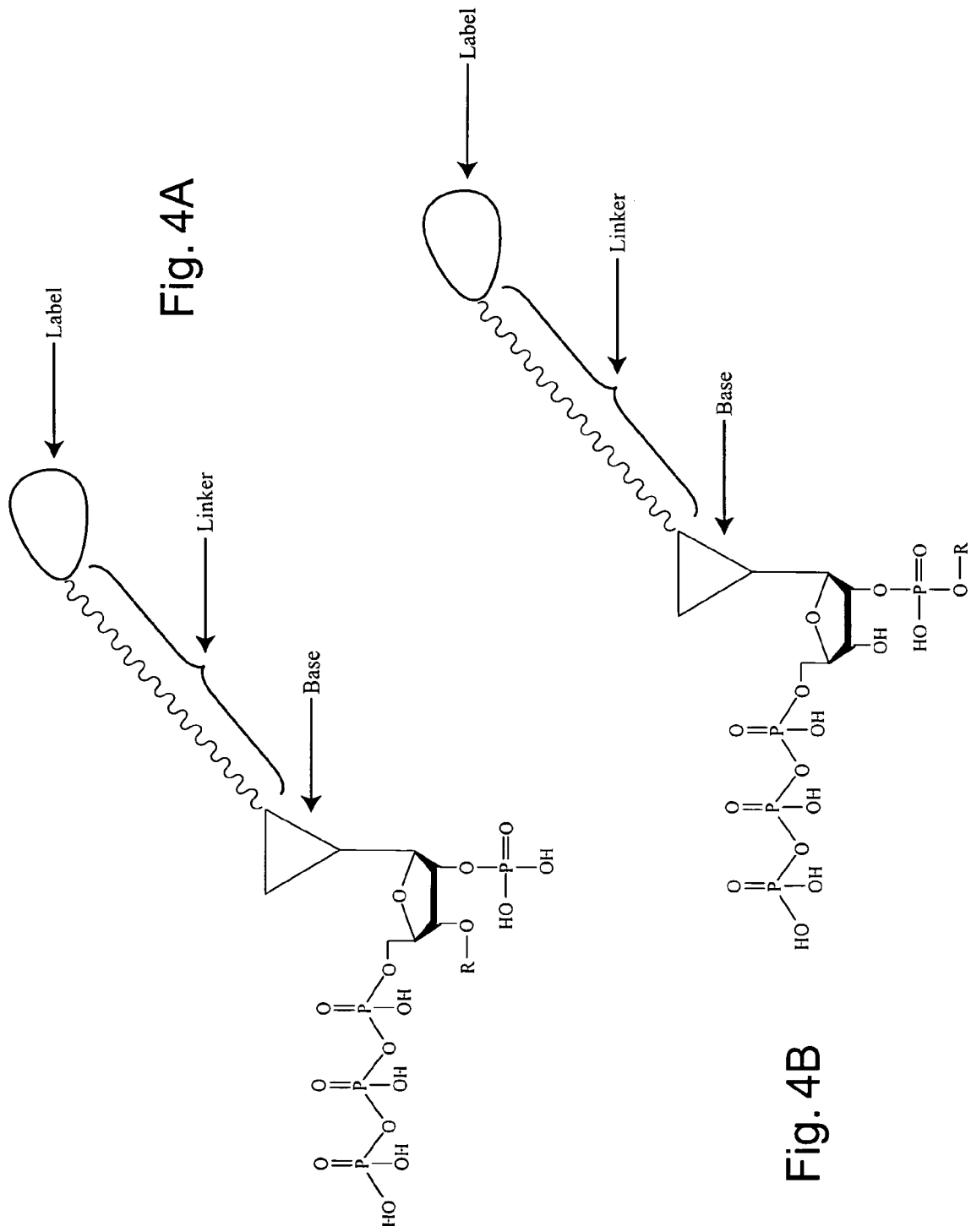

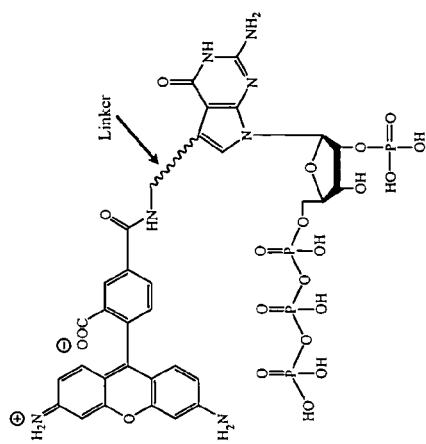
Fig. 6F
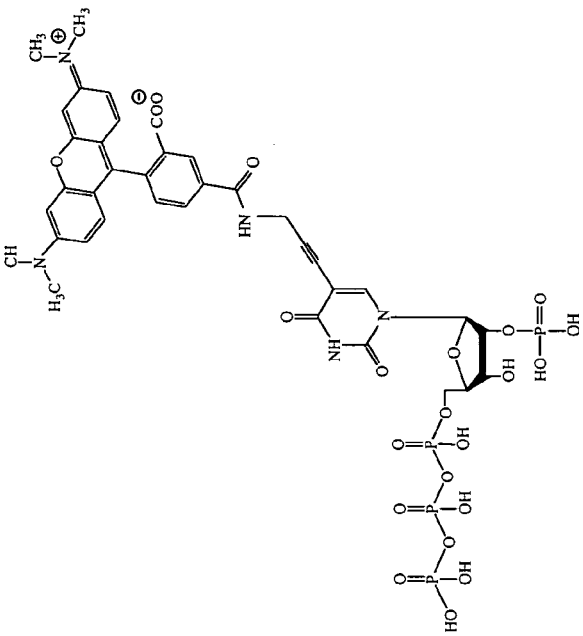
Fig. 6H
Fig. 6E
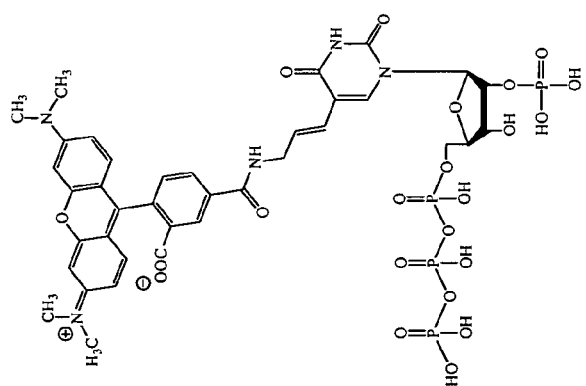
Fig. 6G

SYNTHESIS AND COMPOSITIONS OF 2'-TERMINATOR NUCLEOTIDES

CROSS-REFERENCES TO RELATED APPLICATIONS

This application claims the benefit of U.S. Provisional Application No. 60/483,861, filed Jun. 30, 2003, and 60/519,661, filed Nov. 12, 2003, the disclosures of which are each incorporated by reference in their entirety for all purposes.

COPYRIGHT NOTIFICATION

Pursuant to 37 C.F.R. §1.71(e), Applicants note that a portion of this disclosure contains material, which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates generally to 2'-terminator nucleotides and to methods of their production.

BACKGROUND OF THE INVENTION

Nucleic acid sequencing involves the determination of the sequence of nucleotides of a particular nucleic acid molecule. Knowledge of the sequence of a nucleic acid molecule is typically fundamental to elucidating the function of the molecule and facilitating manipulation of the molecule. Further, variations in individual genomes often account for differences in susceptibility to diseases and pharmacological responses to treatment. To illustrate, changes in a single base of a nucleic acid molecule, which are commonly referred to as single nucleotide polymorphisms (SNPs), can affect an individual's risk for a given disease. By comparing these variations, for example, researchers are gaining an understanding of the medical utility of SNPs, thereby enhancing our ability to effectively diagnose, prognosticate, and treat disease.

Nucleic acid sequencing technology began in the late 1960s with efforts to sequence RNA. In particular, the sequence of 5S-ribosomal RNA from *Escherichia coli* (Brownlee et al. (1967) "Nucleotide sequence of 5S-ribosomal RNA from *Escherichia coli*," *Nature* 215(102):735) and R17 bacteriophage RNA coding for coat protein (Adams et al. (1969) "Nucleotide sequence from the coat protein cistron of R17 bacteriophage RNA," *Nature* 223(210):1009) are some of the early examples of RNA sequencing. Subsequently, Sanger described the sequencing of bacteriophage f1 DNA by primed synthesis with DNA polymerase (Sanger et al. (1973) "Use of DNA polymerase I primed by a synthetic oligonucleotide to determine a nucleotide sequence in phage f1 DNA," *Proc. Natl. Acad. Sci. USA* 70(4): 1209), while Gilbert and Maxam reported on the DNA nucleotide sequence of the lac operator (Gilbert and Maxam (1973) "The nucleotide sequence of the lac operator," *Proc. Natl. Acad. Sci. USA* 70(12):3581).

In 1977, Sanger described the use of modified nucleoside triphosphates (including dideoxyribose) in combination with deoxyribonucleotides to terminate chain elongation (Sanger et al. (1977) "DNA sequencing with chain-terminating inhibitors," *Biotechnology* 24:104). In that same year, Maxam and Gilbert reported a method for sequencing DNA that utilized chemical cleavage of DNA preferentially at guanines, at adenines, at cytosines and thymines equally, and at cytosines alone (Maxam and Gilbert (1977) "A new method for sequencing DNA," *Proc. Natl. Acad. Sci. USA* 74:560). These two methods accelerated manual sequencing based on electrophoretic separation of DNA fragments labeled with radioactive markers and subsequent detection via autoradiography.

The Sanger dideoxy method for sequencing DNA has become far more widely used than the Maxam-Gilbert chemical cleavage method. The Sanger method includes the synthesis of a new strand of DNA starting from a specific priming site and ending with the incorporation of a chain terminating or terminator nucleotide. In particular, a DNA polymerase extends a primer nucleic acid annealed to a specific location on a DNA template by incorporating deoxynucleotides (dNTPs) complementary to the template. Synthesis of the new DNA strand continues until the reaction is randomly terminated by the inclusion of a dideoxynucleotide (ddNTP). These nucleotide analogs are incapable of supporting further chain extension since the ribose moiety of the ddNTP lacks the 3'-hydroxyl necessary for forming a phosphodiester bond with the next incoming dNTP. This produces a population of truncated sequencing fragments, each with a defined or fixed 5'-end and a varying 3'-end. Among the disadvantages of the dideoxy method is the expense associated with making ddNTPs.

Two frequently used automated sequencing methodologies are dye-primer nucleic acid and dye-terminator sequencing. These methods are suitable for use with fluorescent label moieties. Although sequencing can also be done using radioactive label moieties, fluorescence-based sequencing is increasingly preferred. Briefly, in dye-primer sequencing, a fluorescently labeled primer is used in combination with unlabeled ddNTPs. The procedure typically utilizes four synthesis reactions and up to four lanes on a gel for each template to be sequenced (one corresponding to each of the base-specific termination products). Following primer nucleic acid extension, the sequencing reaction mixtures containing dideoxynucleotide-incorporated termination products are routinely electrophoresed on a DNA sequencing gel. Following separation by electrophoresis, the fluorescently-labeled products are excited in the gel with a laser and the fluorescence is detected with an appropriate detector. In automated systems, a detector scans the bottom of the gel during electrophoresis, to detect whatever label moiety has been employed, as the reactions pass through the gel matrix (Smith et al. (1986) "Fluorescence detection in automated DNA sequence analysis," *Nature* 321:674). In a modification of this method, four primers are each labeled with a different fluorescent marker. After the four separate sequencing reactions are completed, the mixtures are combined and the reaction is subjected to gel analysis in a single lane, and the different fluorescent tags (one corresponding to each of the four different base-specific termination products) are individually detected.

Alternatively, dye-terminator sequencing methods are employed. In this method, a DNA polymerase is used to incorporate dNTPs and fluorescently labeled ddNTPs onto the growing end of a DNA primer (Lee et al. (1992) "DNA sequencing with dye-labeled terminators and T7 DNA polymerase: effect of dyes and dNTPs on incorporation of dye-terminators and probability analysis of termination fragments," *Nucleic Acid Res.* 20:2471). This process offers the advantage of not having to synthesize dye-labeled primers. Furthermore, dye-terminator reactions are more convenient in that all four reactions can be performed in the same tube.

Other methods of deconvoluting sequencing reaction mixtures include the use of gas phase ion spectrometry. For example, matrix assisted laser desorption/ionization time-of-flight mass spectrometry (MALDI-TOF-MS) is one approach that has been successfully utilized in high-throughput sequencing and SNP genotyping analyses (see, e.g., Sauer et al. (2002) "Facile method for automated genotyping of single nucleotide polymorphisms by mass spectrometry," *Nucleic Acids Res.* 30(5):e22.

Additional terminator nucleotides of use in sequencing and genotyping nucleic acids are desirable. The present invention provides 2'-terminator nucleotides that are useful in performing sequence determinations in addition to other applications. These and a variety of other features of the invention will be apparent upon a complete review of the following disclosure.

SUMMARY OF THE INVENTION

The invention relates to nucleic acid extension terminators that are economical alternatives to pre-existing terminators. For example, the 2'-terminator nucleotides described herein are readily substituted in various sequencing protocols without sacrificing ease of use. In particular, the 2'-terminator nucleotides of the invention, which have intact sugar rings or sugar analog rings (e.g., carbocyclic rings, etc.), include blocking groups (e.g., negatively charged blocking groups, bulky blocking groups, and/or the like) at 2'-positions of those sugar moieties. Various nucleotide incorporating biocatalysts referred to herein have the ability to extend primer nucleic acids with these 2'-terminator nucleotides (e.g., a 2'-phosphate-3'-hydroxyl NTP or NDP, etc.) at the 3' end of the primer nucleic acids in a template directed manner (i.e., incorporate the 2'-terminator nucleotides into the primer nucleic acids). Certain nucleotide incorporating biocatalysts referred to herein, such as terminal deoxynucleotidyl transferase (TdT; EC 2.7.7.31), polynucleotide phosphorylase (PNPase; EC 2.7.7.8), etc. are able to extend primer nucleic acids in a template independent manner. Upon incorporation of a 2'-terminator nucleotide at the 3'-terminal end of a primer nucleic acid, the nucleic acid is typically rendered non-extendible by a nucleotide incorporating biocatalyst. Furthermore, an extended primer nucleic acid comprising a 2'-terminator nucleotide is also generally resistant to proofreading enzymatic activity (e.g., 3'-5' exonuclease activity, etc.). Thus, the 2'-terminator nucleotides described herein permit the use of proofreading enzymes, e.g., to improve sequence fidelity relative to approaches that utilize catalysts lacking or having diminished proofreading activities. In addition to compositions, the invention also provides methods of producing the 2'-terminator nucleotides described herein.

In one aspect, the invention relates to a composition comprising at least one nucleoside and/or at least one nucleotide (e.g., a 2'-terminator nucleotide) comprising the formula:

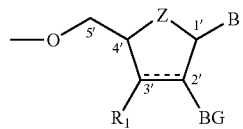

in which $R_1$ is H, OH, a hydrophilic group, or a hydrophobic group; B is at least one homocyclic ring, at least one heterocyclic ring, at least one aryl group, or combinations thereof; BG is a blocking group; Z is O or $CH_2$; and ≈ represents a single or double bond. In addition, the nucleoside and/or nucleotide is typically labeled. Further, the nucleoside and/or nucleotide is also non-extendible by one or more nucleotide incorporating biocatalysts selected from, e.g., G46E E678G CS5 DNA polymerase, a G46E L329A E678G CS5 DNA polymerase, G46E E678G CS6 DNA polymerase, Δ ZO5R DNA polymerase, ZO5 polymerase, E615G Taq DNA polymerase, *Thermus flavus* (Tfl) polymerase (e.g., a modified Tfl polymerase that incorporates the 2'-terminator nucleotides described herein), *Thermatoga maritime*- or Tma-25 polymerase, Tma-30 polymerase, *Thermus thermophilus* (Tth) DNA polymerase, *Thermus* specie SPS-17 polymerase, E615G Taq polymerase, *Thermus* ZO5R polymerase, T7 DNA polymerase, Kornberg DNA polymerase I or *E. coli* DNA Polymerase I, Klenow DNA polymerase, Taq DNA polymerase, Micrococcal DNA polymerase, alpha DNA polymerase, reverse transcriptase, AMV reverse transcriptase, M-MuLV reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase (PNP), ribonucleotide incorporating DNA polymerase, or the like. B and BG each include many different embodiments. Further, at least one of the nucleotide incorporating biocatalysts is generally capable of extending a primer nucleic acid (e.g., in a template independent or dependent manner) to produce an extended primer nucleic acid, incorporating the nucleotide at a terminal end of the extended primer nucleic acid. Typically, the nucleotide comprises 1, 2, 3, or more phosphate groups attached at the 5' position. To illustrate, the nucleotide comprises a 2'-monophosphate-3'-hydroxyl-5'-triphosphate nucleoside in some embodiments of the invention.

Labels (e.g., fluorescent dyes, non-fluorescent dyes, colorimetric labels, mass-modifying groups, radioisotopes, haptens, etc.) are optionally attached (e.g., covalently or non-covalently) to various sites on the nucleotides and nucleosides of the invention. In certain embodiments, for example, a sugar moiety of the nucleoside and/or nucleotide comprises or is attached to the label. In some embodiments, BG comprises or is attached to the label. In other embodiments, B comprises or is attached to the label. Typically, a linker comprises or attaches the label to the nucleoside and/or nucleotide.

The composition optionally further includes one or more extendible nucleotides (e.g., ribonucleotides and/or deoxyribonucleotides). The non-extendible nucleoside and/or nucleotide and the extendible nucleotides are typically present in a molar ratio of 1:1 or less.

In some embodiments, a polymer comprises the nucleoside and/or nucleotide. The polymer optionally comprises, e.g., an oligodeoxynucleotide, an oligoribonucleotide, a polydeoxynucleotide, a polyribonucleotide, an aptamer, an antisense nucleic acid, an RNAi, a DNA-RNA hybrid, a molecular beacon, a nucleic acid probe, a nucleic acid primer, a PNA, a PNA-DNA conjugate, a PNA-RNA conjugate, or the like.

In another aspect, the invention provides a method of producing a labeled, non-extendible nucleotide. The method includes attaching at least one phosphate group to a 5'-position of a sugar moiety of a nucleoside (e.g., a ribonucleoside, a carbocyclic nucleoside, etc.), and attaching at least one blocking group to a 2'-position of the sugar moiety of the nucleoside. The method also includes attaching at least one label to the sugar moiety, the blocking group, and/or a base of the nucleoside, thereby producing the labeled, non-extendible nucleotide, which nucleotide is non-extendible by one or more nucleotide incorporating biocatalysts selected from the group consisting of: G46E E678G CS5 DNA polymerase, a G46E L329A E678G CS5 DNA polymerase, G46E E678G CS6 DNA polymerase, Δ ZO5R DNA polymerase, ZO5 polymerase, E615G Taq DNA polymerase, *Thermus flavus* polymerase, Tma-25 polymerase, Tma-30 polymerase, Tth DNA polymerase, *Thermus* specie SPS-17 polymerase, E615G Taq polymerase, *Thermus* ZO5R polymerase, T7 DNA polymerase, Kornberg DNA polymerase I, Klenow DNA polymerase, Taq DNA polymerase, Micrococcal DNA polymerase, alpha DNA polymerase, reverse transcriptase, AMV reverse transcriptase, M-MuLV reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase, ribonucleotide incorporating DNA polymerase, or the like. In addition, at least one of the nucleotide incorporating biocatalysts is generally capable of extending a primer nucleic acid to produce an extended primer nucleic acid, incorporating the nucleotide at a terminal end of the extended primer nucleic acid. Typically, a linker attaches (e.g., covalently or non-covalently) the label to at least one of: the sugar moiety, the blocking group, or the base of the nucleoside.

The blocking group (or BG) is typically a negatively charged group and/or a bulky group. In some embodiments, for example, the blocking group comprises the formula:

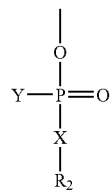

where X is O, S, $NR_3$, $CR_3R_4$, or $SiR_3R_4$; Y is $CR_5R_6R_7$, $SiR_5R_6R_7$, $OR_5$, $SR_5$, or $NHR_5$; $R_2$ is H, OH, $NHR_8$, $SR_8$, an alkyl group, a benzyl group, an aryl group, an alkenyl group, an alkynyl group, an alkoxy group, or combinations thereof; and $R_3$, $R_4$, $R_5$, $R_6$, $R_7$, and $R_8$ are independently selected from H, an alkyl group, a benzyl group, an aryl group, an alkenyl group, an alkynyl group, or combinations thereof. In other embodiments, the blocking group comprises the formula:

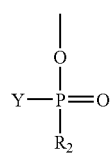

where X is $CR_3R_4R_5$, $SiR_3R_4R_5$, $OR_3$, $SR_3$, or $NHR_3$; $R_2$ is H, OH, $NHR_6$, $SR_6$, an alkyl group, a benzyl group, an aryl group, an alkenyl group, an alkynyl group, an alkoxy group, or combinations thereof; and $R_3$, $R_4$, $R_5$, and $R_6$ are independently selected from H, an alkyl group, a benzyl group, an aryl group, an alkenyl group, an alkynyl group, or combinations thereof.

In still another aspect, the invention provides a method of producing a 2'-monophosphate nucleoside. The method includes reacting a nucleotide comprising the formula:

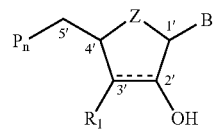

where P is at least one phosphate group; n is an integer greater than 0; $R_1$ is H, OH, a hydrophilic group, or a hydrophobic group; B is at least one homocyclic ring, at least one heterocyclic ring, at least one aryl group, or combinations thereof; Z is O or $CH_2$; and ═══ represents a single or double bond; with trisodium trimetaphosphate $(NaPO_3)_3$ under conditions effective to produce the 2'-monophosphate nucleoside. In certain embodiments, for example, the nucleotide comprises two phosphate groups, whereas in others, the nucleotide comprises three phosphate groups. In some embodiments, the nucleotide and the trisodium trimetaphosphate are reacted in an alkaline solution at a pH of about 14 and/or at room temperature. In certain embodiments, the 2'-monophosphate nucleoside comprises a 2'-monophosphate purine nucleoside that is produced in a mixture comprising a 3'-monophosphate purine nucleoside and the method further comprises separating the 2'-monophosphate purine nucleoside from the 3'-monophosphate purine nucleoside. For example, the 2'-monophosphate purine nucleoside and the 3'-monophosphate purine nucleoside are optionally separated from each other using liquid chromatography and/or another separation technique. In other embodiments, nucleotide synthesis is specific (e.g., regiospecific) or selective (e.g., regioselective). In some embodiments, the 2'-monophosphate nucleoside can include essentially any B so long as it can participate in a base-pairing interaction with another nucleotide, e.g., via hydrogen bonding, a base stacking mechanism, and/or the like. In other embodiments, there is no requirement that B participate in a base-pairing interactions (e.g., in reactions catalyzed by TdT, PNPase, and the like).

Typically, the method also includes labeling the 2'-monophosphate nucleoside with at least one label. For example, the label is typically attached to B of the 2'-monophosphate nucleoside, the sugar moiety of the 2'-monophosphate nucleoside, and/or the 2'-monophosphate of the 2'-monophosphate nucleoside. Optionally, a linker attaches the label to the 2'-monophosphate nucleoside.

BRIEF DESCRIPTION OF THE DRAWINGS

FIGS. 3A-C schematically illustrate dye labeled tetraphosphates according to various embodiments of the invention.

FIGS. 4A and B schematically show labeled nucleotide tetraphosphates according to certain embodiments of the invention.

FIG. 6A-L schematically show various 2'-terminator nucleotides having attached fluorescent dyes according to certain embodiments of the invention.

DETAILED DISCUSSION OF THE INVENTION

I. Definitions

Figure 1B:
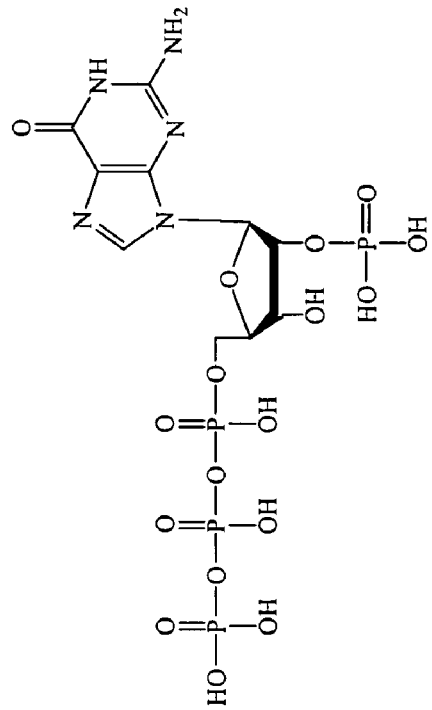
FIGS. 1A-D schematically illustrate 2'-terminator nucleotides according to certain embodiments of the invention.

Before describing the present invention in detail, it is to be understood that this invention is not limited to particular compositions or methods, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

The term "nucleic acid" refers to nucleotides (e.g., ribonucleotides, deoxyribonucleotides, 2'-terminator nucleotides, dideoxynucleotides, etc.) and polymers (e.g., comprising deoxyribonucleoic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), PNA-DNA conjugates, PNA-RNA conjugates, etc.) that comprise such nucleotides covalently linked together, either in a linear or branched fashion.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321), O-methylphophoroamidite linkages (see Eckstein, *Oligonucleotides and Analogues: A Practical Approach*, Oxford University Press (1992)), and peptide nucleic acid backbones and linkages (see, Egholm (1992) *J. Am. Chem. Soc.* 114:1895; Meier et al. (1992) *Chem. Int. Ed. Engl.* 31:1008; Nielsen (1993) *Nature* 365:566; Carlsson et al. (1996) *Nature* 380:207), which references are each incorporated by reference. Other analog nucleic acids include those with positively charged backbones (Denpcy et al. (1995) *Proc. Natl. Acad. Sci. USA* 92: 6097); non-ionic backbones (U.S. Pat. Nos. 5,386,023, 5,637, 684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev. pp* 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

An "oligonucleotide" refers to a nucleic acid that includes at least two nucleotides, typically more than three nucleotides, and more typically greater than ten nucleotides. The exact size of an oligonucleotide generally depends on various factors, including the ultimate function or use of the oligonucleotide. Oligonucleotides are optionally prepared by any suitable method, including, for example, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103: 3185-3191; automated synthesis methods; or the solid support method of U.S. Pat. No. 4,458,066, among other methods known in the art, which references are each incorporated by reference.

A "primer nucleic acid" is typically a nucleic acid that can hybridize to a template nucleic acid and permit chain extension or elongation using, e.g., a nucleotide incorporating biocatalyst, such as a thermostable polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. A primer nucleic acid can be labeled, if desired, by incorporating a label detectable by, e.g., spectroscopic, photochemical, biochemical, immunochemical, or chemical techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. In addition, a primer nucleic acid can simply provide a substrate for a nucleotide incorporating biocatalyst in a template independent manner.

An "extended primer nucleic acid" refers to a primer nucleic acid to which one or more additional nucleotides have been added or otherwise incorporated (e.g., covalently bonded to).

A "template nucleic acid" refers to a nucleic acid to which a primer nucleic acid can hybridize and be extended. Accordingly, template nucleic acids include subsequences that are at least partially complementary to the primer nucleic acids. Template nucleic acids can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template nucleic acids optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto. As used herein, a "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extendible nucleotide" refers to a nucleotide to which at least one other nucleotide can be added or covalently bonded, e.g., in a reaction catalyzed by a nucleotide incorporating biocatalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide.

A "non-extendible" nucleotide refers to a nucleotide, which upon incorporation into a nucleic acid prevents further extension of the nucleic acid, e.g., by at least one nucleotide incorporating biocatalyst.

A "2'-terminator nucleotide" refers to a nucleotide analog that comprises a blocking group (BG) at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst selected from, e.g., a G46E E678G CS5 DNA polymerase, a G46E E678G CS6 DNA polymerase, a Δ ZO5R polymerase, an E615G Taq DNA polymerase, a *Thermus flavus* polymerase, a Tma-25 polymerase, a Tma-30 polymerase, a Tth DNA polymerase, a *Thermus* specie SPS-17 polymerase, an E615G Taq polymerase, a *Thermus* ZO5R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, a M-MuLV reverse transcriptase, a DNA polymerase, an RNA polymerase, an *E. coli* RNA polymerase, a SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and/or the like. An exemplary blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are also described further herein.

A "tetraphosphate nucleotide" refers to a nucleotide that includes four phosphate groups. Exemplary tetraphosphate nucleotides include 2'-monophosphate-5'-triphosphate nucleosides and 3'-monophosphate-5'-triphosphate nucleosides.

A "negatively charged blocking group" refers to a blocking group that comprises at least one negative charge, which negative charge at least contributes to the non-extendible property of the nucleotide to which it is attached, e.g., by electrostatic repulsion of incoming nucleotides. To illustrate, negatively charged blocking groups at the 2'-positions of nucleotides of the invention optionally include phosphate, carboxy, or other groups referred to herein that typically comprise at least one negative charge upon ionization. In certain embodiments, multiple factors can contribute to the non-extendible property of a nucleotide of the invention including, e.g., blocking group charge and size.

A "bulky blocking group" refers to a blocking group comprising sufficient size to sterically hinder the incorporation of an incoming nucleotide, thereby at least contributing to the non-extendible property of the nucleotide to which the blocking group is attached. As noted above, in some embodiments of the invention, multiple factors can contribute to the non-extendible property of a 2'-terminator nucleotide including, e.g., blocking group charge and size.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety, and one or more phosphate groups.

A "mass modifying" group modifies the mass, typically measured in terms of molecular weight as daltons, of a molecule that comprises the group. For example, mass modifying groups that increase the discrimination between at least two nucleic acids with single base differences in size or sequence can be used to facilitate sequencing using, e.g., molecular weight determinations.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane, cycloheptane, cyclohexene, and the like.

An "alkyl group" refers to a linear, branched, or cyclic saturated hydrocarbon moiety and includes all positional isomers, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, and the like. An alkenyl group typically comprises about 1-20 carbon atoms and more typically comprises about 2-15 carbon atoms. Alkenyl groups can be substituted or unsubstituted.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. An alkynyl group typically comprises about 1-20 carbon atoms and more typically comprises about 2-15 carbon atoms. Alkynyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

A "halo group" refers to a group that comprises a halogen atom, such as F, Cl, Br, or I.

An "aryl group" refers to a substituent group of atoms or moiety that is derived from an aromatic compound. Exemplary aryl groups include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties.

An "ether group" refers to a linear, branched, or cyclic moiety that comprises two carbon atoms attached to a single oxygen atom. Exemplary ether groups include, e.g., methoxymethyl, methoxyethyl, methoxypropyl, ethoxyethyl, and the like.

A "thioether group" refers to a linear, branched, or cyclic moiety that comprises two carbon atoms attached to a single sulfur atom and includes, e.g., methylthiomethyl, methylthioethyl, methylthiopropyl, and the like.

An "alkylamine group" refers to an amino group that comprises at least one alkyl group.

An "alkenylamine group" refers to an amino group that comprises at least one alkenyl group.

An "alkynylamine group" refers to an amino group that comprises at least one alkynyl group.

An "ester group" refers to a class of organic compounds that includes the general formula RCOOR', where R and R' are independently selected from an alkyl group, an alkenyl group, an alkynyl group, an aryl group, or combinations thereof.

A "polyaminoacid" refers to compound or group that comprises two or more amino acid residues. Exemplary polyaminoacids include peptides, polypeptides, proteins, and the like.

A "heterooligo" refers to an oligonucleotide that comprises two or more different nucleotide residues.

A "heterooligo/polyaminoacid group" refers to a hybrid group that comprises both at least one heterooligo moiety and at least one polyaminoacid moiety.

An "aldehyde group" refers to an organic group that includes the formula CHO.

An "alcohol group" refers to an organic group that includes at least one hydroxy group.

A "silyl group" refers to a class of compounds that includes the general formula $SiRR^1R^2$, where R, $R^1$, and $R^2$ are independently an H, an alkyl group, an alkenyl group, an alkynyl group, an aryl group, or a combination of such groups.

A reaction or series of reactions is described as "selective" if it yields a predominance (i.e., a majority but less than 100%) of one isomeric product over other possible isomeric products. To illustrate, a reaction or series of reactions that produces a predominance of a 2'-monophosphate-3'-hydroxyl-5'-triphosphate nucleoside over a 3'-monophosphate-2'-hydroxyl-5'-triphosphate nucleoside is selective. The term "specific" is used if one isomeric product is formed exclusively in a reaction or series of reactions.

A "sequence" of a nucleic acid refers to the order and identity of nucleotides in the nucleic acid. A sequence is typically read in the 5' to 3' direction.

A "full-length sequence" refers to a nucleic acid sequence that comprises at least substantially the same number of nucleotides as a reference sequence or a nucleic acid sequence that is at least partially complementary to the reference sequence. In certain embodiments of the invention, for example, an extended primer nucleic acid is complementary to a full-length sequence of a template nucleic acid or other reference sequence.

A "subsequence" or "fragment" refers to any portion of an entire nucleic acid sequence.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

The term "attached" refers to interactions including, but not limited to, covalent bonding, ionic bonding, chemisorption, physisorption, and combinations thereof.

A "linker" refers to a chemical moiety that covalently or non-covalently (e.g., ionically, etc.) attaches a compound or substituent group to, e.g., a solid support, another compound or group, or the like. For example, a linker optionally attaches a label (e.g., a fluorescent dye, a radioisotope, etc.) to a 2'-terminator nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, Pljevaljcic et al. (2003) *J. Am. Chem. Soc.* 125(12):3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes").

A "thermostable enzyme" refers to an enzyme that is stable to heat (i.e., resists breakdown or denaturation) and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are both incorporated by reference. As used herein, a thermostable polymerase is typically suitable for use in a temperature cycling reaction such as the polymerase chain reaction ("PCR"). For a thermostable nucleotide incorporating enzyme, enzymatic activity refers to the catalysis of the combination of the nucleotides in the proper manner to form primer extension products that are complementary to a template nucleic acid. Other thermostable enzymes referred to herein, include thermostable pyrophosphatases, which similarly retain sufficient activity when subjected to elevated temperatures, e.g., to minimize pyrophosphorolysis. Similarly to enzymes, DNAzymes and ribozymes may also be thermostable.

A "modified" enzyme refers to an enzyme comprising a monomer sequence in which at least one monomer of the sequence differs from a monomer in a reference sequence, such as a native or wild-type form of the enzyme or another modified form of the enzyme, e.g., when the two sequences are aligned for maximum identity. Exemplary modifications include monomer insertions, deletions, and substitutions. The modified enzymes (i.e., protein- or nucleic acid-based catalysts) of the invention have been or are optionally created by various diversity generating methods. Although essentially any method can be used to produce a modified enzyme, certain exemplary techniques include recombining (e.g., via recursive recombination, synthetic recombination, or the like) two or more nucleic acids encoding one or more parental enzymes, or by mutating one or more nucleic acids that encode enzymes, e.g., using recursive ensemble mutagenesis, cassette mutagenesis, random mutagenesis, in vivo mutagenesis, site directed mutagenesis, or the like. A nucleic acid encoding a parental enzyme typically includes a gene that, through the mechanisms of transcription and translation, produces an amino acid sequence corresponding to a parental enzyme, e.g., a native form of the enzyme. Modified enzymes also include chimeric enzymes that have identifiable component sequences (e.g., structural and/or functional domains, etc.) derived from two or more parents. Also included within the definition of modified enzymes are those comprising chemical modifications (e.g., attached substituent groups, altered substituent groups, etc.) relative to a reference sequence. Similarly to enzymes, DNAzymes and ribozymes may also comprise similar modifications.

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, weakly fluorescent labels, non-fluorescent labels, calorimetric labels, chemiluminescent labels, bioluminescent labels, radioactive labels, mass-modifying groups, antibodies, antigens, biotin, haptens, and enzymes (including, e.g., peroxidase, phosphatase, etc.).

II. 2'-Terminator Nucleosides and Nucleotides

The present invention relates to methods of producing, and compositions comprising, 2'-terminator nucleotides and/or nucleosides. In brief, the nucleotides and/or nucleosides of the invention typically include a hydroxyl group at a 3'-position of an intact sugar ring and a blocking group (e.g., a negatively charged blocking group, a bulky blocking group, and/or the like) at a 2'-position of the sugar moiety. Certain nucleotide incorporating biocatalysts described herein comprise the ability to extend primer nucleic acids with these 2'-terminator nucleotides in a template directed manner. Upon incorporation of a 2'-terminator nucleotide at a 3'-terminal end of a primer nucleic acid, the nucleic acid is typically rendered non-extendible by the nucleotide incorporating biocatalyst. Thus, the terminator nucleotides of the invention can be used to produce sequencing ladders and for 3'-labeling among other applications. Furthermore, an extended primer nucleic acid comprising a 2'-terminator nucleotide is generally resistant to proofreading enzymatic activity (e.g., 3'-5' exonuclease activity, etc.). As a consequence, a nucleotide incorporating biocatalyst utilized in, e.g., a nucleic acid sequencing protocol that utilizes the terminator nucleotides of the invention can include a 3'-5' exonuclease activity or "proof reading" activity, e.g., to improve sequence fidelity relative to approaches that utilize catalysts that lack or have a diminished proofreading activities. Additional details relating to sequencing methods, systems, and other aspects related to the nucleotides and nucleosides of the invention are provided in, e.g., U.S. Provisional Patent Application No. 60/483,861, entitled "2'-TERMINATOR NUCLEOTIDE-RELATED METHODS AND SYSTEMS," filed Jun. 30, 2003 by Gelfand et al., which is incorporated by reference.

Nucleosides and nucleotides of the invention generally include the formula:

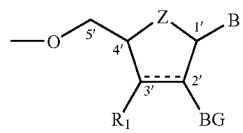

in which $R_1$ is H, OH, a hydrophilic group, or a hydrophobic group; B is at least one homocyclic ring, at least one heterocyclic ring (with or without exocyclic heteroatoms), at least one aryl group, or combinations thereof; BG is a blocking group; Z is O or $CH_2$; and ═══ represents a single or double bond. In addition, a nucleoside or nucleotide of the invention is typically labeled. Further, a nucleotide of the invention generally comprises 1, 2, 3, or more phosphate groups attached at the 5' position. In one embodiment of the invention, for example, the nucleotide comprises a 2'-monophosphate-3'-hydroxyl-5'-triphosphate nucleoside.

Figure 1D:
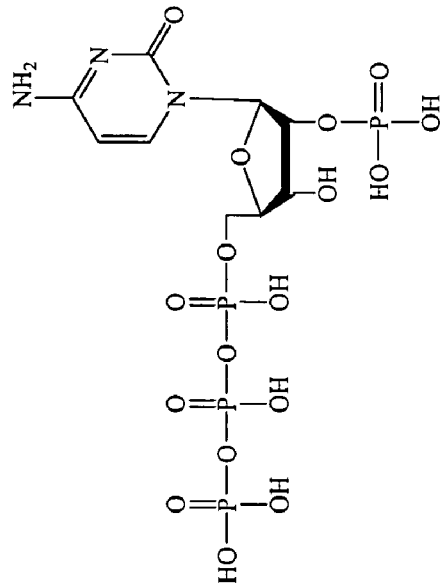
Figure 1A:
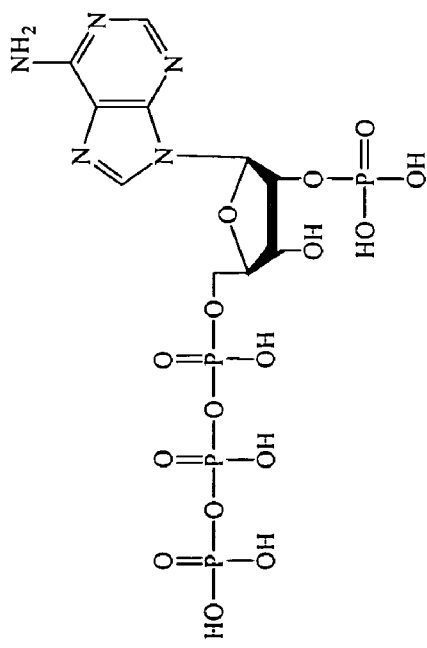
Figure 1C:
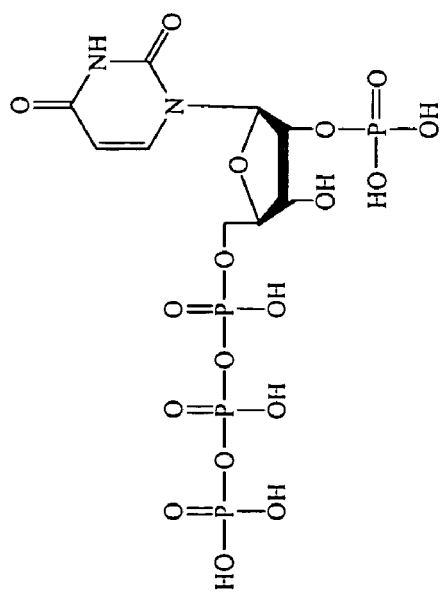

FIGS. 1A-D schematically illustrate 2'-terminator nucleotides according to certain embodiments of the invention. In particular, FIG. 1A schematically shows an adenosine tetraphosphate terminator nucleotide, FIG. 1B schematically depicts a guanosine tetraphosphate terminator nucleotide, FIG. 1C schematically illustrates a uridine tetraphosphate terminator nucleotide, and FIG. 1D schematically shows a cytidine tetraphosphate terminator nucleotide.

A. Bases

Essentially any heterocyclic ring or aryl group (i.e., as the base or B group) that can base pair with another nucleic acid, e.g., via a hydrogen bond or through a base stacking mechanism is optionally included at the 1' position of the sugar moiety of the nucleosides and nucleotides of the invention. Accordingly, no attempt is made herein to describe all of the possible groups that can be utilized. However, certain representative B groups are provided to further illustrate the invention. In some embodiments, for example, B comprises the formula:

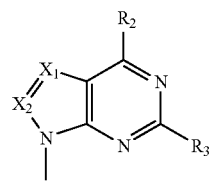

where $X_1$ and $X_2$ are independently selected from CH and N; $R_2$ is H, OH, or $NR_4R_5$; $R_3$ is H, OH, or $NR_6R_7$; $R_4$ and $R_5$ are independently selected from H, an alkyl group, an alkenyl group, an alkynyl group, a benzyl group, an aryl group, an aryloxy group, and combinations thereof; and, $R_6$ and $R_7$ are independently selected from H, an alkyl group, an alkenyl group, an alkynyl group, a benzyl group, an aryl group, an aryloxy group, and combinations thereof. In other embodiments, B comprises the formula:

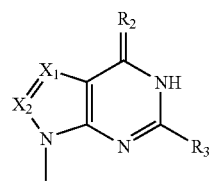

where $X_1$ and $X_2$ are independently selected from CH and N; $R_2$ is O or S; $R_3$ is H, OH, or $NR_4R_5$; and $R_4$ and $R_5$ are independently selected from H, an alkyl group, an alkenyl group, an alkynyl group, a benzyl group, an aryl group, an aryloxy group, and combinations thereof. In some embodiments, B comprises the formula:

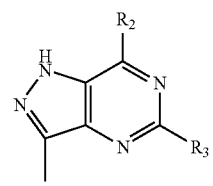

where $R_2$ is H, OH, or $NR_4R_5$; $R_3$ is H, OH, or $NR_6R_7$; $R_4$ and $R_5$ are independently selected from H, an alkyl group, an alkenyl group, an alkynyl group, a benzyl group, an aryl group, an aryloxy group, and combinations thereof; and, $R_6$ and $R_7$ are independently selected from H, an alkyl group, an alkenyl group, an alkynyl group, a benzyl group, an aryl group, an aryloxy group, and combinations thereof. In some embodiments, B comprises the formula:

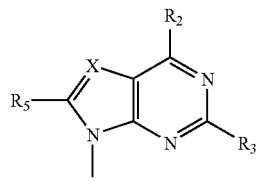

where X is CH or N; $R_2$ and $R_3$ are independently selected from H, OH, and $NHR_4$; $R_4$ is H, an alkyl group, an alkenyl group, an alkynyl group, a benzyl group, an aryl group, an aryloxy group, or combinations thereof; and, $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof. In other embodiments, B comprises the formula:

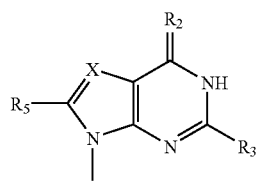

where X is CH or N; $R_2$ is O or S; $R_3$ is H, OH, or $NHR_4$; $R_4$ is H, an alkyl group, an alkenyl group, an alkynyl group, a benzyl group, an aryl group, an aryloxy group, or combinations thereof; and $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof. In certain embodiments, B comprises the formula:

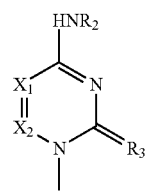

where $X_1$ and $X_2$ are independently selected from CH and N; $R_2$ is H, an alkyl group, an alkenyl group, an alkynyl group, a benzyl group, an aryl group, an aryloxy group, or combinations thereof; and $R_3$ is O or S. In other embodiments, B comprises the formula:

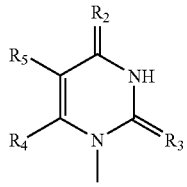

where $R_2$ and $R_3$ are independently selected from O and S; and $R_4$ and $R_5$ are independently selected from H, $NH_2$, SH, OH, an alkyl group, an alkenyl group, an alkynyl group, a benzyl group, an aryl group, an aryloxy group, an alkoxy group, a halo group, and combinations thereof. In some embodiments, B comprises the formula:

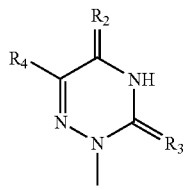

where $R_2$ and $R_3$ are independently selected from O and S; and $R_4$ is H, $NH_2$, SH, OH, an alkyl group, an alkenyl group, an alkynyl group, a benzyl group, an aryl group, an aryloxy group, an alkoxy group, a halo group, or combinations thereof. In other embodiments, B comprises the formula:

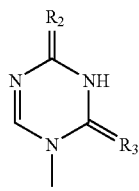

where $R_2$ and $R_3$ are independently selected from O and S. In some embodiments, B comprises the formula:

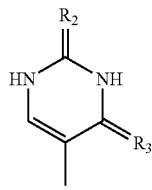

where $R_2$ and $R_3$ are independently selected from O and S. In other embodiments, B comprises the formula:

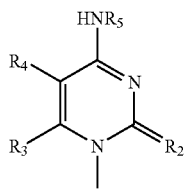

where $R_2$ is O or S; $R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and $R_5$ is an alkyl group, an alkoxy group, an alkenyl group, an alkenoxy group, an alkynyl group, an alkynoxy group, an aryl group, an aryloxy group, a benzyl group, a benzyloxy group, or combinations thereof.

B. Blocking Groups

Figure 2B:
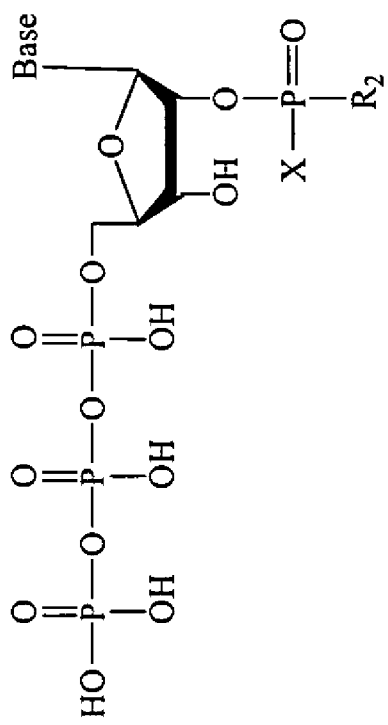
FIGS. 2A and B schematically show 2'-terminator nucleotides according to some embodiments of the invention.
Figure 2A:
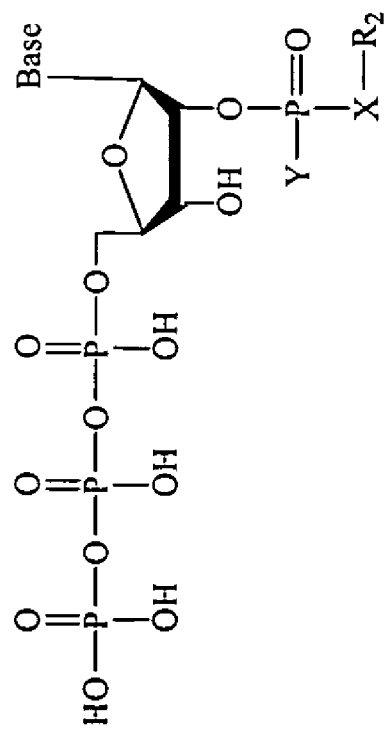

The blocking groups (BG) utilized at the 2' position of the sugar moiety also include various embodiments. In some embodiments, for example, BG is a negatively charged group and/or a bulky group. To further illustrate, BG is optionally selected from, e.g., CN, $NO_2$, $N_3$, a silyl group, a halo group, an alcohol group, an ether group, an aldehyde group, an acidic group, an ester group, an amino group, and combinations thereof. More specifically, BG optionally comprises the formula:

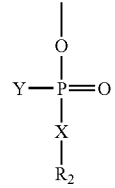

where X is O, S, $NR_3$, $CR_3R_4$, or $SiR_3R_4$; Y is $CR_5R_6R_7$, $SiR_5R_6R_7$, $OR_5$, $SR_5$, or $NHR_5$; $R_2$ is H, OH, $NHR_8$, $SR_8$, an alkyl group, a benzyl group, an aryl group, an alkenyl group, an alkynyl group, an alkoxy group, or combinations thereof; and $R_3$, $R_4$, $R_5$, $R_6$, $R_7$, and $R_8$ are independently selected from H, an alkyl group, a benzyl group, an aryl group, an alkenyl group, an alkynyl group, or combinations thereof. FIG. 2A schematically depicts one nucleotide comprising a blocking group having this formula. To further illustrate, BG optionally comprises the formula:

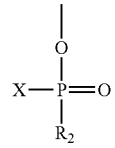

where X is $CR_3R_4R_5$, $SiR_3R_4R_5$, $OR_3$, $SR_3$, or $NHR_3$; $R_2$ is H, OH, $NHR_6$, $SR_6$, an alkyl group, a benzyl group, an aryl group, an alkenyl group, an alkynyl group, an alkoxy group, or combinations thereof; and $R_3$, $R_4$, $R_5$, and $R_6$ are independently selected from H, an alkyl group, a benzyl group, an aryl group, an alkenyl group, an alkynyl group, or combinations thereof. FIG. 2B schematically depicts one 2'-terminator nucleotide comprising a blocking group having this formula.

C. Labeling

The 2'-terminator nucleic acids of the invention typically comprise at least one label. For example, the label is optionally attached, e.g., to a homocyclic ring, a heterocyclic ring, or an aryl group of a 2'-terminator nucleotide (e.g., via $C^5$ of a pyrimidine, $N^4$ of cytidine, $N^7$ of a purine, $N^6$ of adenosine, $C^8$ of a purine, or another attachment site known in the art), e.g., through an amide, ester, thioester, ether, thioether, carbon-carbon, or other type of covalent bond. In addition, or alternatively, the label is attached to a sugar moiety (e.g., a ribose sugar, etc.), or an analog thereof (e.g., a carbocyclic ring, etc.), of a 2'-terminator nucleotide, and/or a phosphate group of a 2'-terminator nucleotide, such as by a covalent bond that is an amide, ester, thioester, ether, thioether, carbon-carbon, or other bond. Covalent bonds are typically formed in reactions between electrophilic and nucleophilic groups of labels and nucleotides of the invention. In certain embodiments, labels and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, phosphorous-nitrogen bonds, etc.). Optionally, a linker attaches the label to a 2'-terminator nucleotide. A wide variety of linkers can be used or adapted for use in conjugating labels and nucleotides. Certain non-limiting illustrations of such linkers are referred to herein.

Figure 5:
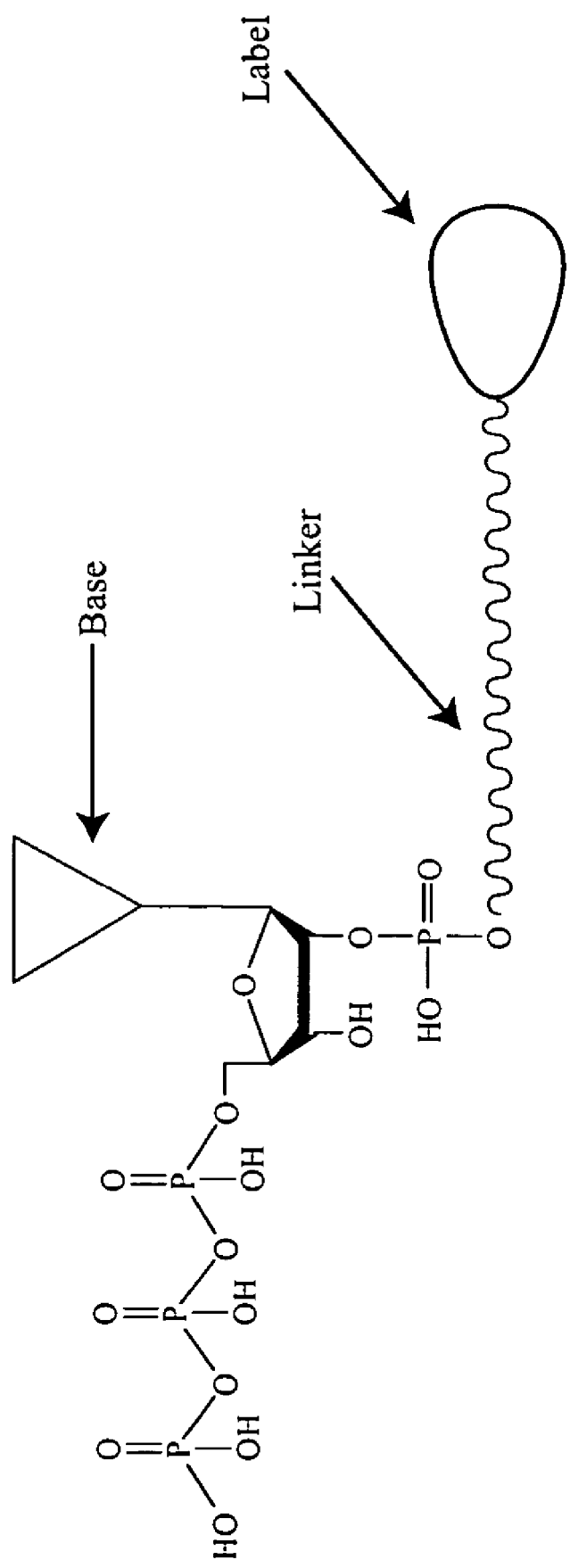
FIG. 5 schematically depicts a label attached to a nucleotide tetraphosphate via a linker according to one embodiment of the invention.
Figure 6A:
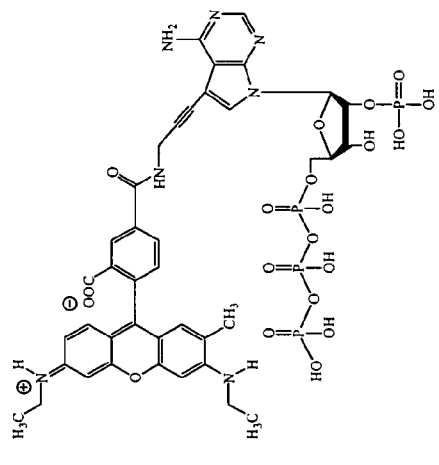
Figure 6B:
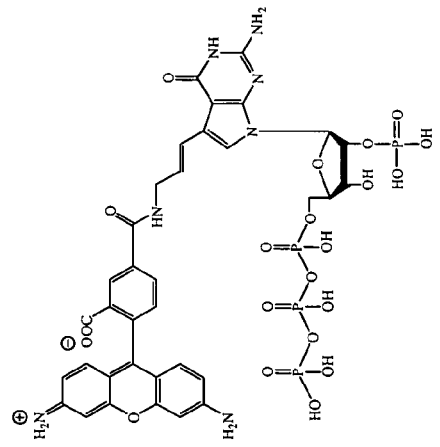
Figure 6C:
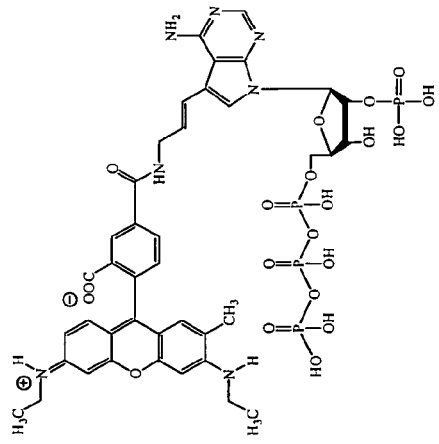
Figure 6D:
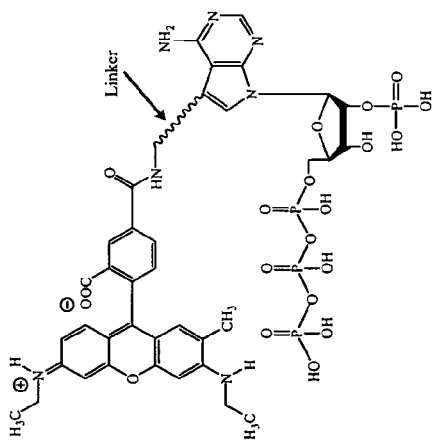
Figure 6J:
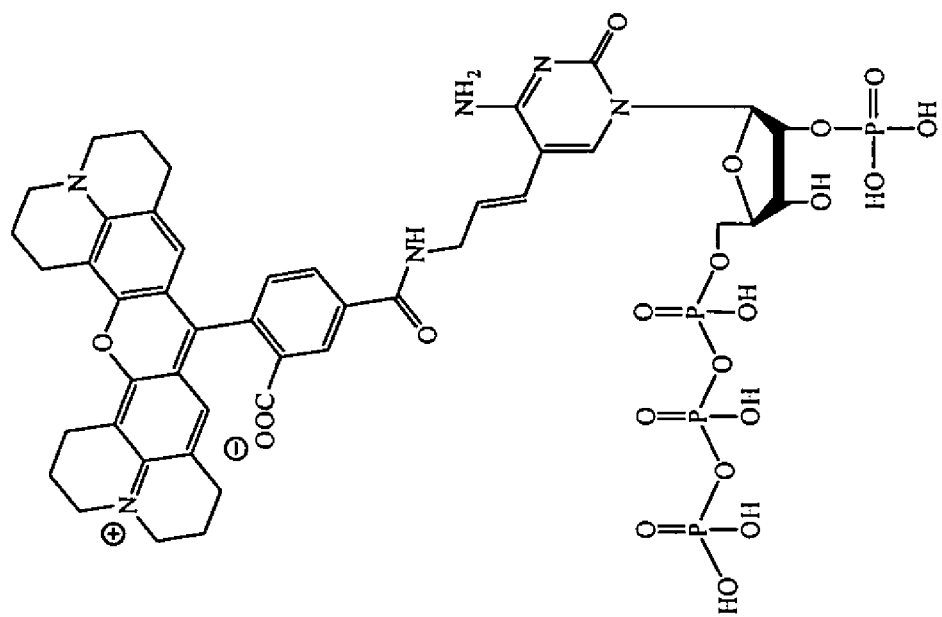
Figure 6I:
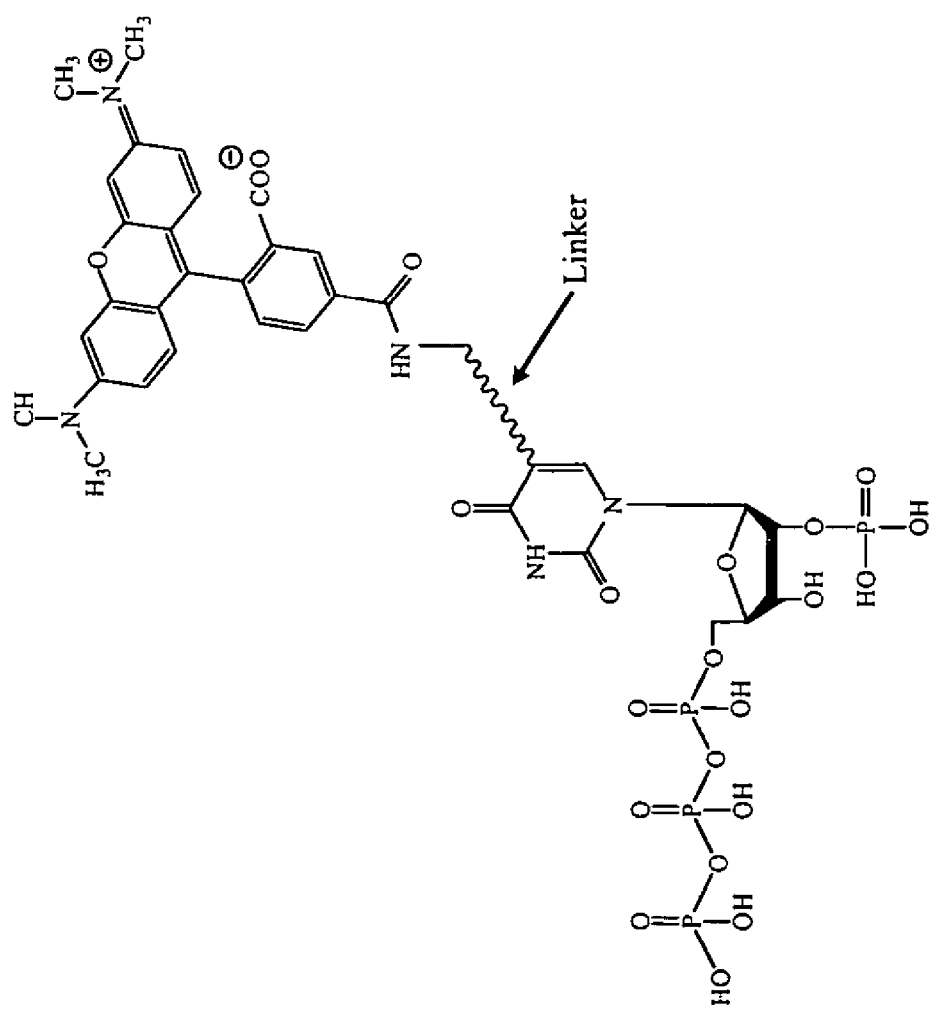
Figure 6L:
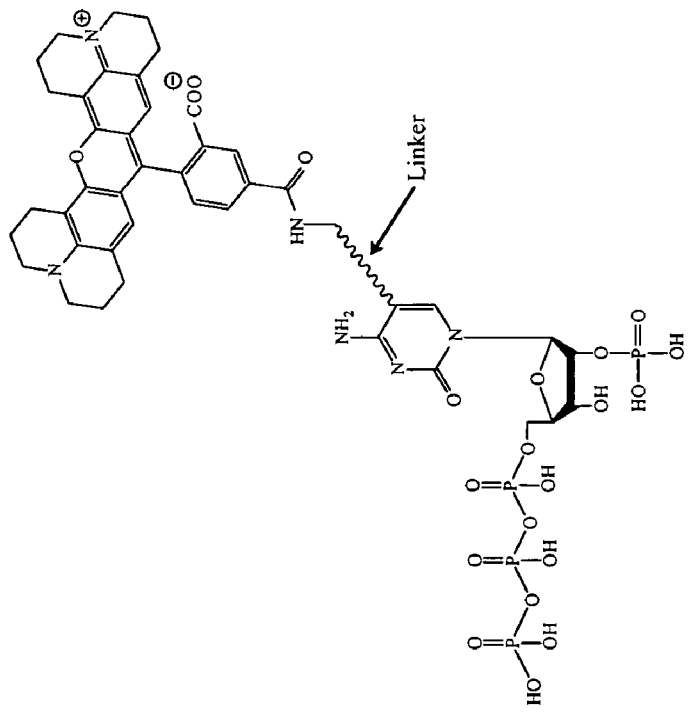
Figure 6K:
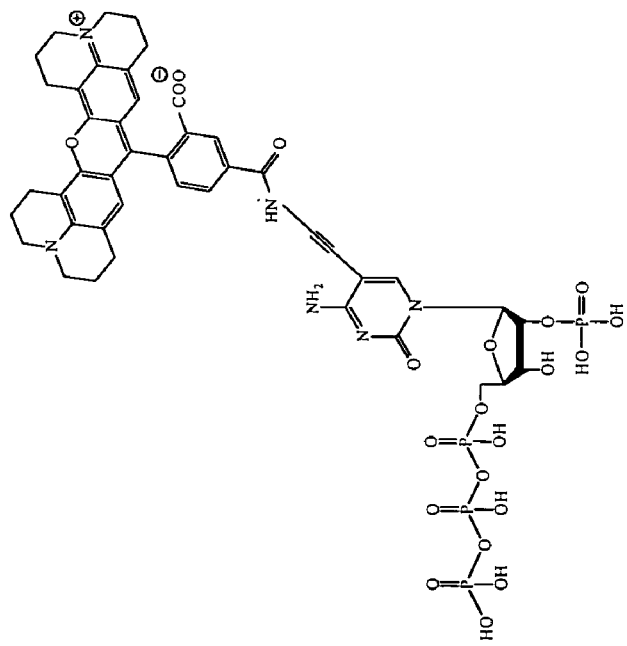
Figure 7:
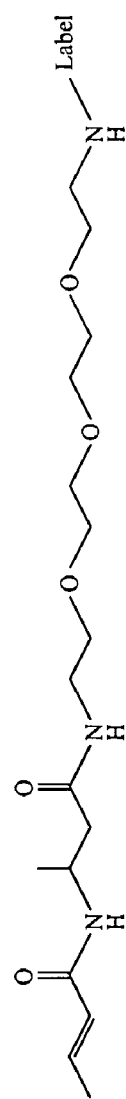
FIG. 7 schematically depicts a linker according to one embodiment of the invention.

To further illustrate, FIGS. 3A-C schematically shows dye labeled tetraphosphates according to certain embodiments of the invention. In particular, FIG. 3A schematically shows a reporter dye attached to a base of a 2'-terminator nucleotide via a linker group, FIG. 3B schematically depicts a reporter dye attached to a blocking group of a 2'-terminator nucleotide via a linker group, and FIG. 3C schematically shows a reporter dye attached to a sugar moiety of a 2'-terminator nucleotide via a linker group, where X is H, OH, $NHR_1$, $SR_1$, an alkyl group, a benzyl group, an aryl group, an alkyl-aryl group, an alkenyl group, an alkynyl group, an alkoxy group, or the like (where $R_1$ is H, an alkyl group, a benzyl group, an aryl group, an alkyl-aryl group, an alkenyl group, an alkynyl group, or the like), or comprises O, S, N, C, or the like, Y is $OR_2$, $SR_2$, $NHR_2$, or the like (where $R_2$ is H, an alkyl group, an alkenyl group, an alkynyl group, an aryl group, an alkyl-aryl group, or the like), and Z comprises O, S, N, C, Si, or the like. FIGS. 4A and B also schematically show labeled nucleoside tetraphosphates according to some embodiments of the invention. More specifically, FIGS. 4A and B schematically show labels attached via linkers to bases of the nucleoside tetraphosphates, where R is selected from, e.g., H, OH, an alkyl group, an aryl group, an alkyl-aryl group, an alkenyl group, an alkynyl group, and the like. In addition, FIG. 5 schematically depicts a label attached to a nucleoside tetraphosphate via a linker according to one embodiment of the invention. FIGS. 6A-L also schematically show various 2'-terminator nucleotides having fluorescent dyes attached to the bases of the nucleotides according to certain embodiments of the invention. In particular, FIGS. 6A-C schematically show R6G-labeled adenosine tetraphosphates, FIGS. 6D-F schematically depict R110-labeled guanosine tetraphosphates, FIG. 6G-I schematically illustrate TAMRA-labeled uridine tetraphosphates, and FIGS. 6J-L schematically show ROX-labeled cytidine tetraphosphates. Of course, labels may be attached to 2'-terminator nucleotides at other locations, as described herein, including via linkers. To illustrate, FIG. 7 schematically depicts one embodiment of a linker. In some embodiments, for example, the 2'-terminator nucleotides of FIGS. 6C, 6F, 6I, and 6L include the linker of FIG. 7.

Essentially any label is optionally utilized to label the nucleotides and nucleosides of the invention. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIG-DYE™ v 2 dyes, BIGDYE™ v 3 dyes, etc.), Lucifer dyes (e.g., Lucifer yellow, etc.), CASCADE BLUE®, Oregon Green, and the like. Additional details relating to fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128 (5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference.

In certain embodiments, the label comprises a radioisotope, such as $^3H$, $^{14}C$, $^{22}Na$, $^{32}P$, $^{33}P$, $^{35}S$, $^{42}K$, $^{45}Ca$, $^{59}Fe$, $^{125}I$, $^{203}Hg$, or the like. To further exemplify, the label also optionally includes at least one mass-modifying group. For example, the mass-modifying group is optionally selected from, e.g., deuterium, F, Cl, Br, I, S, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNY_2$, $CH_2CONY_2$, $(CH_2)_nOH$, $CH_2F$, $CHF_2$, $CF_3$, and a phosphorothioate group, where X is O, NH, NY, S, NHC(S), $OCO(CH)_nCOO$, $NHCO(CH_2)_nCOO$, $OSO_2O$, $OCO(CH_2)_n$, NHC(S)NH, $OCO(CH_2)_nS$, $OCO(CH_2)S$, $NC_4O_2H_2S$, OPO(O-alkyl), or OP(O-alkyl); n is an integer from 1 to 20 inclusive; and, Y is H, deuterium, an alkyl group, an alkoxy group, an aryl group, a polyoxymethylene group, a monoalkylated polyoxymethylene group, a polyethylene imine group, a polyamide group, a polyester group, a alkylated silyl group, a heterooligo, a polyaminoacid, a heterooligo/polyaminoacid group, or a polyethylene glycol group. Additional details relating to nucleic acid labeling and sequence analysis are provided in, e.g., Sterky et al. (2000) "Sequence analysis of genes and genomes," *J. Biotech.* 76(2000):1, Sensen (Ed.) *Biotechnology, Volume 5B, Genomics and Bioinformatics*, John Wiley & Sons, Inc. (2001), and Sensen (Ed.) *Essentials of Genomics and Bioinformatics*, John Wiley & Sons, Inc. (2002), which are each incorporated by reference.

A large variety of linkers are available for linking labels to nucleic acids and will be apparent to one of skill in the art. A linker is generally of a structure that is sterically and electronically suitable for incorporation into a nucleic acid. Linkers optionally include, e.g., ether, thioether, carboxamide, sulfonamide, urea, urethane, hydrazine, or other moieties. To further illustrate, linkers generally include between about one and about 25 nonhydrogen atoms selected from, e.g., C, N, O, P, Si, S, etc., and comprise essentially any combination of, e.g., ether, thioether, amine, ester, carboxamide, sulfonamide, hydrazide bonds and aromatic or heteroaromatic bonds. In some embodiments, for example, a linker comprises a combination of single carbon-carbon bonds and carboxamide or thioether bonds. Although longer linear segments of linkers are optionally utilized, the longest linear segment typically contains between about three to about 15 nonhydrogen atoms, including one or more heteroatoms.

Nonlimiting examples of linker moieties include substituted (e.g., functionalized) or unsubstituted groups, such as imidazole/biotin linkers, polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine, etc.), and the like. Certain of these and other linkers are described further in, e.g., U.S. Pat. No. 6,339,392 to Haugland et al., U.S. Pat. No. 5,047,519 to Hobbs, Jr. et al., U.S. Pat. No. 4,711,958 to Iizuka et al., U.S. Pat. No. 5,175,269 to Stavrianopoulos, U.S. Pat. No. 4,711,955 to Ward et al., U.S. Pat. No. 5,241,060 to Engelhardt et al., U.S. Pat. No. 5,328,824 to Ward et al., and U.S. Pat. Publication No. 2002/0151711 by Khan et al., which are each incorporated by reference. Additional details relating to nucleic acid labeling and linkers are provided in, e.g., Hermanson, *Bioconjugate Techniques*, Elsevier Science (1996), which is incorporated by reference. In certain embodiments, suitable linkers comprise photocleavable moieties, such as 2-nitrobenzyl moieties, alpha-substituted 2-nitrobenzyl moieties (e.g., 1-(2-nitrophenyl) ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Photocleavable linkers are described further in, e.g., U.S. Pat. Publication No. 2003/0099972 by Olejnik et al., which is incorporated by reference. In some embodiments, linkers include metals, such as platinum atoms. These are described further in, e.g., U.S. Pat. No. 5,714,327 to Houthoff et al., which is incorporated by reference. A number of linkers of varying lengths are commercially available from various suppliers including, e.g., Qiagen-Operon Technologies, Inc. (Alameda, Calif.), BD Biosciences Clontech (Palo Alto, Calif.), and Molecular Bio-Sciences (Boulder, Colo.).

III. Synthesis

The invention also provides various methods of synthesizing the nucleotides and nucleosides described herein. For example, one method of producing a labeled, non-extendible nucleotide includes attaching at least one phosphate group to a 5'-position of a sugar moiety of a nucleoside (e.g., a ribonucleoside, a carbocyclic nucleoside, etc.), and attaching at least one blocking group to a 2'-position of the sugar moiety of the nucleoside. Exemplary blocking groups and bases that are optionally included in the nucleosides utilized in this method are described herein. The method also includes attaching at least one label to the sugar moiety, the blocking group, and/or a base of the nucleoside. Suitable labels are described further above and in certain examples provided below.

In addition, the invention also provides methods of producing 2'-monophosphate nucleoside that include reacting a nucleotide comprising the formula:

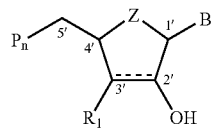

where P is at least one phosphate group; n is an integer greater than 0; $R_1$ is H, OH, a hydrophilic group, or a hydrophobic group; B is at least one homocyclic ring, at least one heterocyclic ring, at least one aryl group, or combinations thereof; Z is O or $CH_2$; and ==represents a single or double bond; with trisodium trimetaphosphate $(NaPO_3)_3$ under conditions effective to produce the 2'-monophosphate nucleoside. In certain embodiments, for example, the nucleotide comprises two phosphate groups, whereas in others, the nucleotide comprises three phosphate or more groups. Effective conditions to produce the nucleotide generally include performing the reactions in solution at an alkaline pH. For example, the synthesis is typically performed at a pH greater than about 8.0, more typically at a pH greater than about 10.0, and still more typically at a pH greater than about 12.0 (e.g., at about 12.5, 13.0, 13.5, or 14.0). Various basic compounds can be used to adjust the pH of the reaction mixture including, e.g., KOH and NaOH among many others that are widely known in the art. The nucleotide is typically the limiting reagent. Although other temperature conditions are optionally utilized, these synthesis reactions are generally performed at or near room temperature (i.e., between about 20° C. and about 30° C., e.g., at about 23° C., 24° C., 25° C., 26° C., etc.). In addition, these reactions are generally allowed to proceed for at least about 4 hours, typically for at least about 6 hours, and even more typically for at least about 16 hours.

Figure 8:
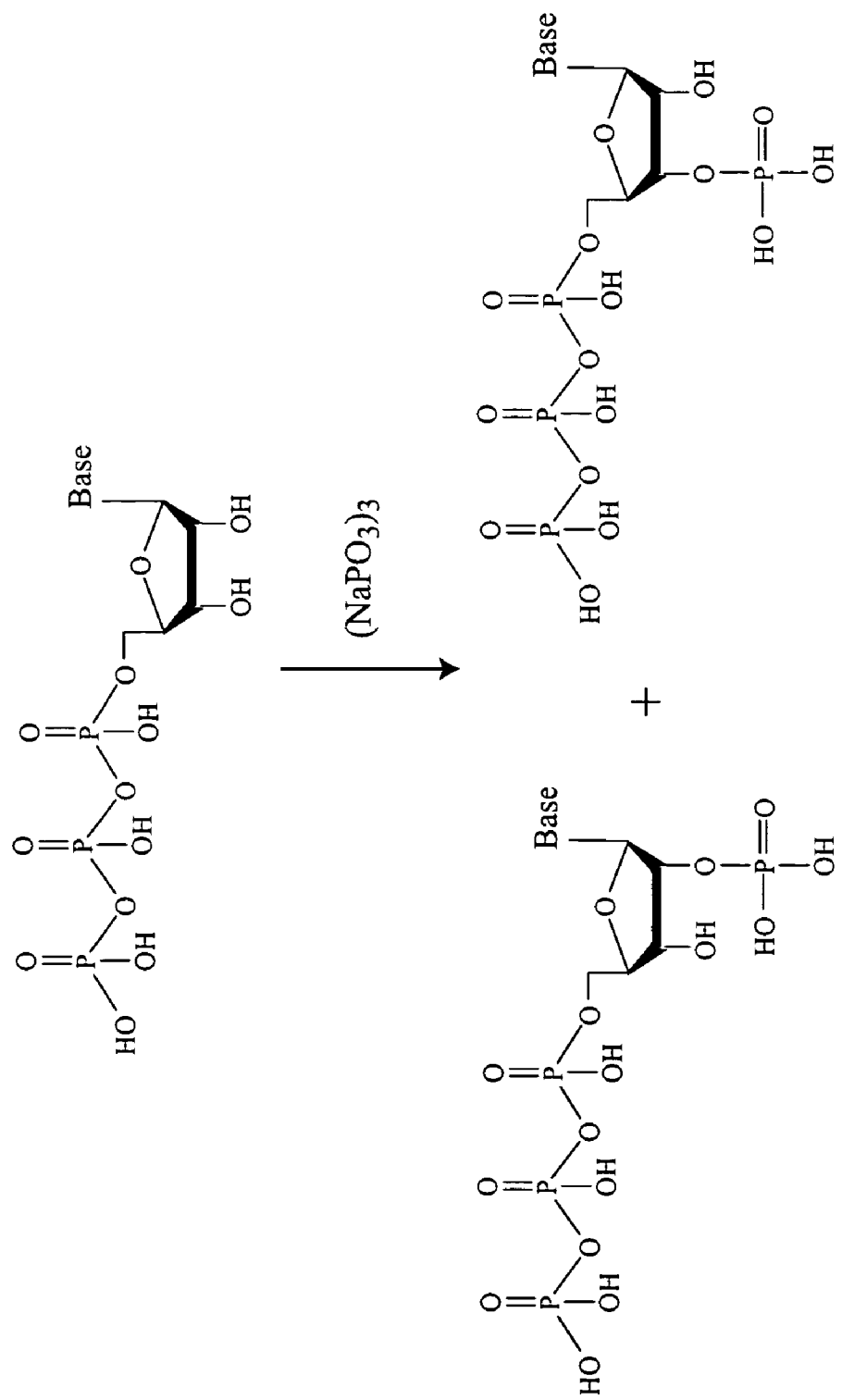
FIG. 8 schematically illustrates a synthetic reaction that produces a mixture of 5'-triphosphate-3'-monophosphate nucleotides and 5'-triphosphate-2'-monophosphate nucleotides according to one embodiment of the invention.

To further illustrate the methods of the invention, FIG. 8 schematically illustrates a synthetic reaction that produces a mixture of 5'-triphosphate-3'-monophosphate nucleosides and 5'-triphosphate-2'-monophosphate nucleosides (e.g., in molar ratios of about 50:50). The synthesis of a mixture of purine nucleotides is provided below in an example. Specific or at least selective synthesis pathways are also described herein. In embodiments where a mixture of nucleotides is produced, the methods typically further include separating the 5'-triphosphate-2'-monophosphate nucleosides from the 5'-triphosphate-3'-monophosphate nucleosides. A variety of separation techniques can be utilized to separate 5'-triphosphate-2'-monophosphate nucleosides from other compounds or impurities including liquid chromatography. Various separation techniques that are useful in purifying nucleotide synthesis products are described further in, e.g., Skoog et al., *Principles of Instrumental Analysis*, 5th Ed., Harcourt Brace College Publishers (1998) and Currell, *Analytical Instrumentation: Performance Characteristics and Quality*, John Wiley & Sons, Inc. (2000), which are both incorporated by reference. In addition, many polymerases, such as G46E E678G CS5 DNA polymerases, G46E E678G CS6 DNA polymerases, and Δ Z05R polymerases do not incorporate, e.g., 5'-triphosphate-3'-monophosphate-2'-deoxynucleosides into primer nucleic acids in primer extension reactions, so the mixtures produced by these methods are optionally not separated prior to such subsequent usage. This typically reduces production costs associated with nucleotide synthesis relative to those processes that include product separation steps. However, the separation of components in these mixtures can also provide certain benefits. To illustrate, in embodiments where both nucleotide products are labeled, the separation of the two nucleotides prior to usage can minimize background signal upon detection by eliminating, e.g., the labeled 3'-monophosphate-2'-deoxynucleoside from the sample. Further, reagent costs are typically reduced when only the 2'-terminator nucleotide product is labeled. Accordingly, product separation provides for such selective labeling.

As mentioned above, the invention also provides regiospecific or at least regioselective synthetic pathways such that product purification is generally minimized, if not entirely eliminated. These synthetic pathways, which typically include the use of various protecting groups (e.g., TBDMS, SiR, TOM, BOC, etc.) at the 3'-position of sugar moieties, are described further below.

Figure 9:
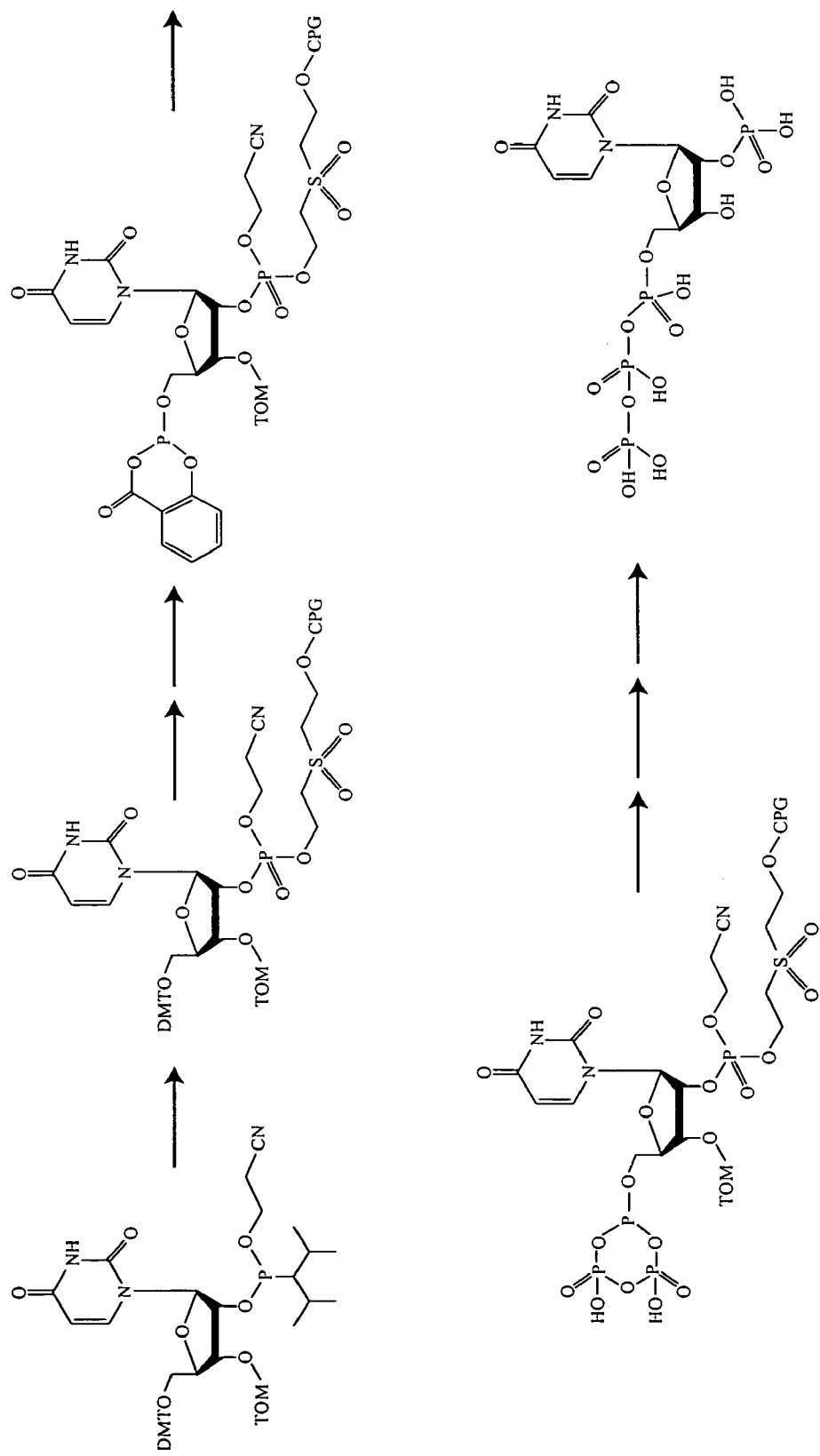
FIG. 9 schematically depicts certain steps in a solid phase synthesis pathway for a uridine tetraphosphate according to one embodiment of the invention.
Figure 10:
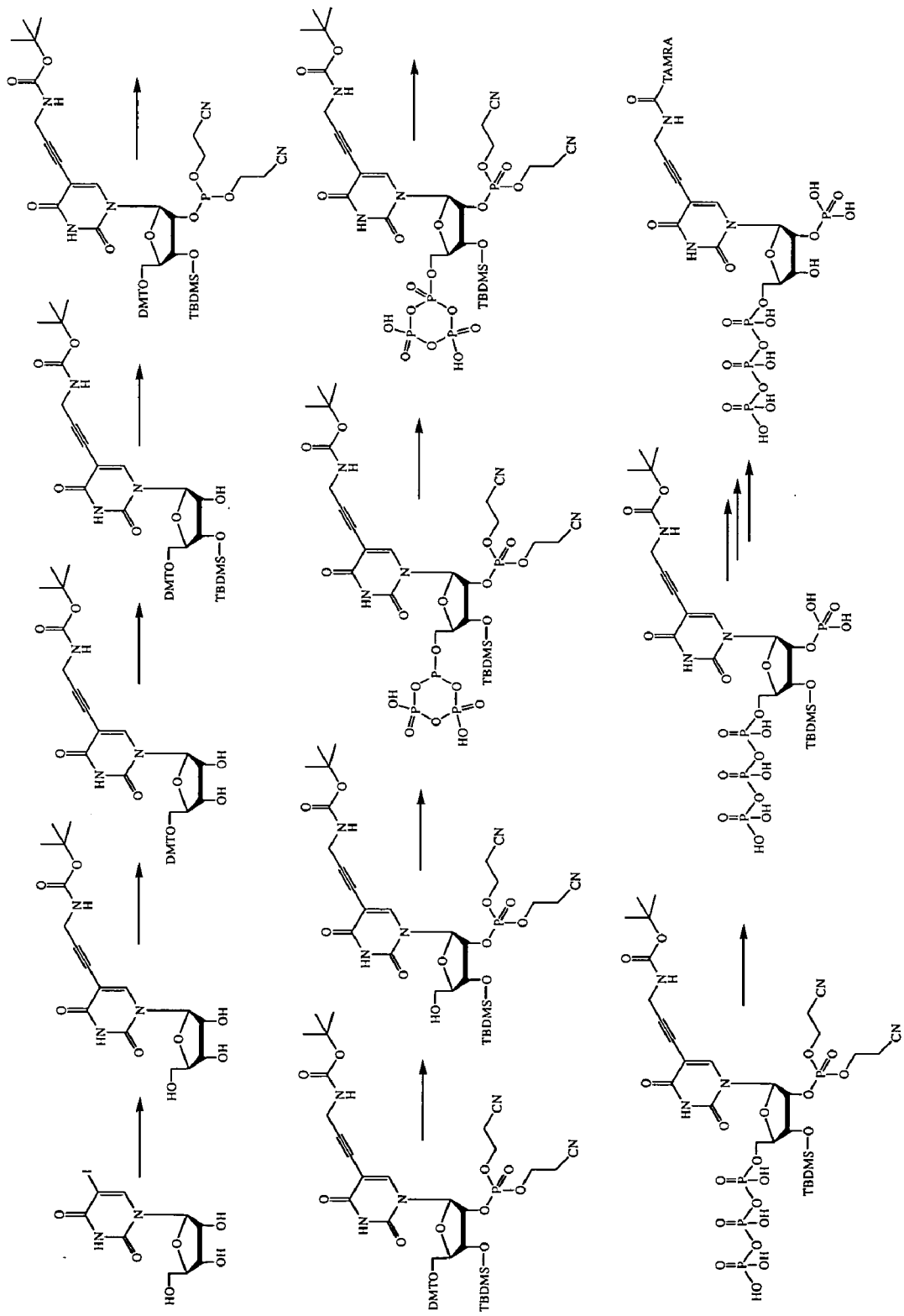
FIG. 10 schematically shows certain steps in a regiospecific synthesis pathway for TAMRA-uridine tetraphosphate according to one embodiment of the invention.

The synthetic pathways of the invention are further illustrated in, e.g., FIG. 9, which schematically depicts certain steps in a solid phase synthesis pathway for a uridine tetraphosphate according to one embodiment of the invention. In addition, FIG. 10 schematically shows certain steps in a regiospecific synthesis pathway for TAMRA-uridine tetraphosphate according to one embodiment of the invention. Additional synthetic pathways and other aspects related to the production of the nucleotides of the invention are provided in the examples below.

Various synthetic techniques that can be adapted for use in the synthesis protocols of the present invention are generally known and described in, e.g., March, *Advanced Organic Chemistry: Reactions, Mechanisms, and Structure*, 4th Ed., John Wiley & Sons, Inc. (1992), and Carey and Sundberg, *Advanced Organic Chemistry Part A: Structure and Mechanism*, 4th Ed., Plenum Press (2000), which are each incorporated by reference. Chemical starting materials and other reaction components useful in the synthesis of the nucleotides of the present invention are readily available from various commercial suppliers including, e.g., Sigma-Aldrich, Inc. (St Louis, Mo.).

IV. Nucleotide Incorporating Biocatalysts

Figure 11:
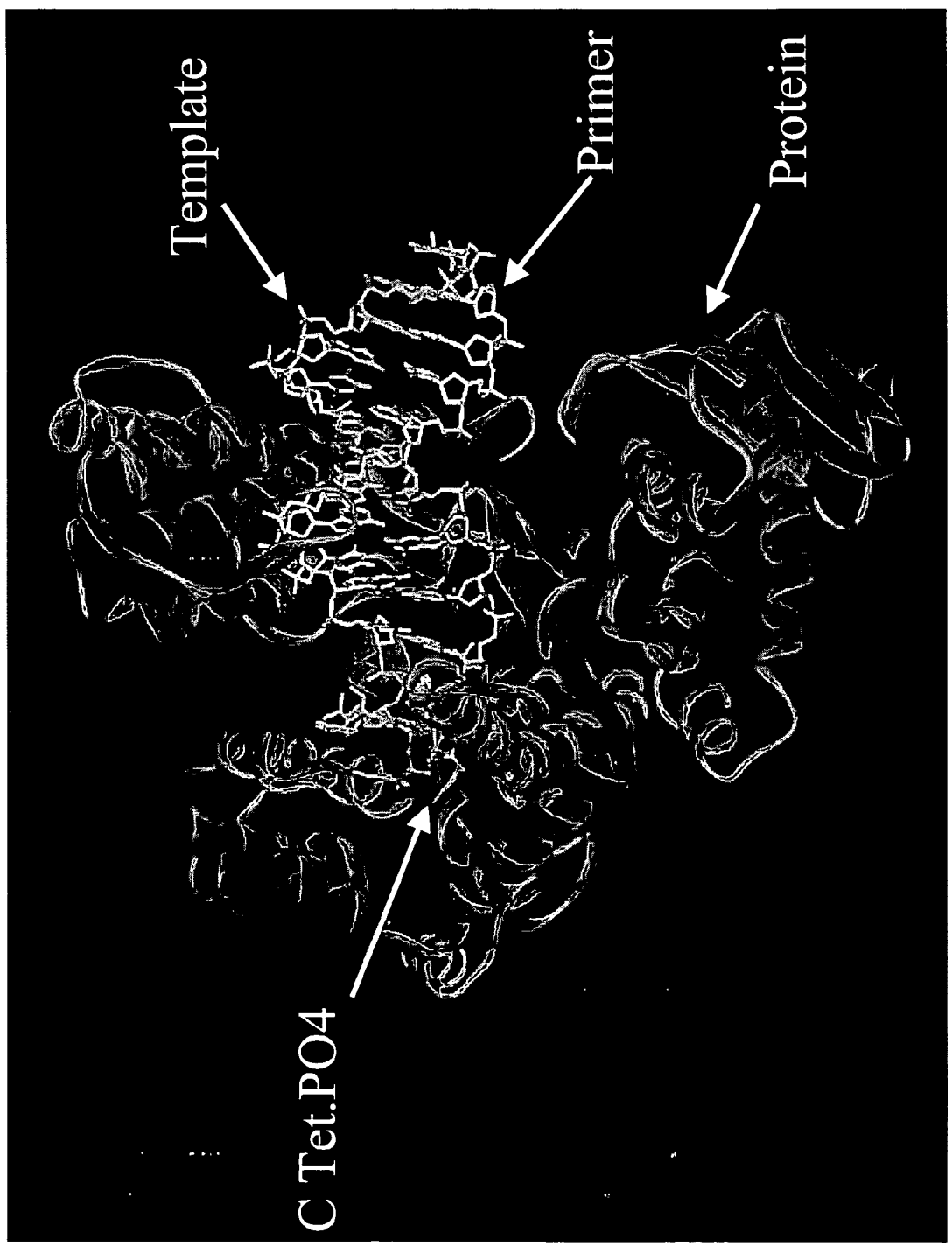
FIG. 11 schematically illustrates a polymerase bound to a template nucleic acid and to a primer nucleic acid with an incorporated cytidine tetraphosphate nucleotide of the invention.

Upon incorporating a nucleotide of the present invention into a nucleic acid, the nucleic acid is typically rendered non-extendible by at least one nucleotide incorporating biocatalyst selected from, e.g., G46E E678G CS5 DNA polymerase, a G46E L329A E678G CS5 DNA polymerase, G46E E678G CS6 DNA polymerase, Δ Z05R polymerase, E615G Taq DNA polymerase, T7 DNA polymerase, Kornberg DNA polymerase I, Klenow DNA polymerase, Taq DNA polymerase, Micrococcal DNA polymerase, alpha DNA polymerase, AMV reverse transcriptase, M-MuLV reverse transcriptase, reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase, ribonucleotide incorporating DNA polymerase, and the like. Thus, the 2'-terminator nucleotides of the invention can be used in nucleic acid sequencing, 3' labeling, and the like. The sequences of certain of these nucleotide incorporating biocatalysts are publicly available from various sources including, e.g., GenBank® and the like. To further illustrate aspects of the invention, FIG. 11 schematically depicts a polymerase bound to a template nucleic acid and to a primer nucleic acid with an incorporated cytidine tetraphosphate nucleotide of the invention.

One type of polymerase that can incorporate, but which generally cannot extend, a 2'-terminator nucleotide of the invention lacks an F to Y mutation in helix O of the enzyme or otherwise lacks a mutation that enhances incorporation of 3'-deoxynucleotides by the enzyme. Optionally, the enzyme comprises a 3'-5' exonuclease activity and/or is a thermostable enzyme. The enzyme is typically derived from an organism, such as *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax, Bacillus stearothermophilus*, or the like.

In some embodiments, the enzyme is modified. Exemplary modified enzymes include, e.g., a G46E E678G CS5 DNA polymerase, a G46E L329A E678G CS5 DNA polymerase, a G46E E678G CS6 DNA polymerase, a Δ Z05R polymerase, an E615G Taq DNA polymerase, and the like. These modified enzymes generally comprise an increased ability to incorporate 2'-terminator nucleotides relative to an unmodified enzyme. That is, the modified enzymes typically comprise mutations that enhance that incorporation of ribonucleotides, that enhance incorporation of 2'-modified analogs of ribonucleotides, and/or that reduce or eliminate 5'-3' exonuclease activity, e.g., relative to an enzyme that lacks one or more of these mutations. Additional details relating to useful nucleotide incorporating biocatalysts are also provided in, e.g., U.S. Pat. No. 5,939,292, entitled "THERMOSTABLE DNA POLYMERASES HAVING REDUCED DISCRIMINATION AGAINST RIBO-NTPS," which issued Aug. 17, 1999 to Gelfand et al., U.S. Pat. No. 4,889,818, entitled "PURIFIED THERMOSTABLE ENZYME," which issued Dec. 26, 1989 to Gelfand et al., U.S. Pat. No. 5,374,553, entitled "DNA ENCODING A THERMOSTABLE NUCLEIC ACID POLYMERASE ENZYME FROM *THERMOTOGA MARITIMA*," which issued Dec. 20, 1994 to Gelfand et al., U.S. Pat. No. 5,420,029, entitled "MUTATED THERMOSTABLE NUCLEIC ACID POLYMERASE ENZYME FROM *THERMOTOGA MARITIMA*," which issued May 30, 1995 to Gelfand et al., U.S. Pat. No. 5,455,170, entitled "MUTATED THERMOSTABLE NUCLEIC ACID POLYMERASE ENZYME FROM *THERMUS* SPECIES Z05," which issued Oct. 3, 1995 to Abramson et al., U.S. Pat. No. 5,466,591, entitled "5' TO 3' EXONUCLEASE MUTATIONS OF THERMOSTABLE DNA POLYMERASES," which issued Nov. 14, 1995 to Abramson et al., U.S. Pat. No. 5,618,711, entitled "RECOMBINANT EXPRESSION VECTORS AND PURIFICATION METHODS FOR *THERMUS THERMOPHILUS* DNA POLYMERASE," which issued Apr. 8, 1997 to Gelfand et al., U.S. Pat. No. 5,624,833, entitled "PURIFIED THERMOSTABLE NUCLEIC ACID POLYMERASE ENZYME FROM *THERMOTOGA MARITIMA*," which issued Apr. 29, 1997 to Gelfand et al., U.S. Pat. No. 5,674,738, entitled "DNA ENCODING THERMOSTABLE NUCLEIC ACID POLYMERASE ENZYME FROM *THERMUS* SPECIES Z05," which issued Oct. 7, 1997 to Abramson et al., U.S. Pat. No. 5,789,224, entitled "RECOMBINANT EXPRESSION VECTORS AND PURIFICATION METHODS FOR *THERMUS THERMOPHILUS* DNA POLYMERASE," which issued Aug. 4, 1998 to Gelfand et al., U.S. Pat. No. 5,795,762, entitled "5' TO 3' EXONUCLEASE MUTATIONS OF THERMOSTABLE DNA POLYMERASES," which issued Aug. 18, 1998 to Abramson et al., U.S. Pat. Application Publication No. US 2002/0012970, entitled "HIGH TEMPERATURE REVERSE TRANSCRIPTION USING MUTANT DNA POLYMERASES," which published Jan. 31, 2002 by Smith et al., and U.S. patent application Ser. No. 10/401,403, filed Mar. 26, 2003, which are each incorporated by reference.

The production of modified enzymes with, e.g., enhanced efficiency for incorporating 2'-terminator nucleotides may be accomplished by various processes including, e.g., site-directed mutagenesis, chemical modification, etc. More specifically, site-directed mutagenesis is generally accomplished by site-specific primer-directed mutagenesis. This technique is typically conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. To further illustrate, many other approaches to modify nucleic acids, such as "recombinant PCR" methods can also be utilized.

In practicing aspects of the present invention (e.g., producing modified enzymes, performing sequencing reactions, etc.), many conventional techniques in molecular biology and recombinant DNA are optionally utilized. These techniques are well known and are explained in, for example, *Current Protocols in Molecular Biology*, Volumes I, II, and III, 1997 (F. M. Ausubel ed.); Sambrook et al., 2001, *Molecular Cloning: A Laboratory Manual*, Third Edition, Cold Spring Harbor Laboratory Press, Cold Spring Harbor, N.Y.; Berger and Kimmel, *Guide to Molecular Cloning Techniques Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively).

V. Kits

The 2'-terminator nucleotides of the invention are typically provided in kits, e.g., for extending primer nucleic acids in sequencing reactions, for performing end labeling reactions, and the like. The kits generally include a nucleotide incorporating biocatalyst as described herein in addition to 2'-terminator nucleotides. For example, the 2'-terminator nucleotides optionally include labels (e.g., radioisotopes, fluorescent dyes, mass-modifying groups, or the like). In some embodiments, kits further include extendible nucleotides and optionally, at least one of the extendible nucleotides comprises a label as described herein. Optionally, the kits further include at least one pyrophosphatase (e.g., a thermostable pyrophosphatase), e.g., for use in minimizing pyrophosphorolysis, uracil N-glycosylase (UNG) (e.g., a thermolabile UNG), e.g., for use in applications where protection against carry-over contamination is desirable. Typically, the kits also include a set of instructions for extending the primer nucleic acids with the nucleotide incorporating biocatalyst and the 2'-terminator nucleotides. Further, the kits typically also include containers for packaging the nucleotide incorporating biocatalyst, the 2'-terminator nucleotides, the set of instructions, and/or other kit components. To further illustrate, kits of the invention optionally include one or more pre-made reaction mixtures that comprise one or more extendible nucleotides, one or more 2'-terminator nucleotides, a buffer, and one or more nucleotide incorporating biocatalysts. In certain embodiments, kits further include template nucleic acids and/or primer nucleic acids (e.g., labeled primer nucleic acids). Optionally, the template nucleic acids or the primer nucleic acids are attached to a solid support.

The following examples are offered by way of illustration only and are not intended to limit the scope of the claimed invention.

EXAMPLES

Example I

Regiospecific Synthesis of Uridine Tetraphosphate

Figure 12:
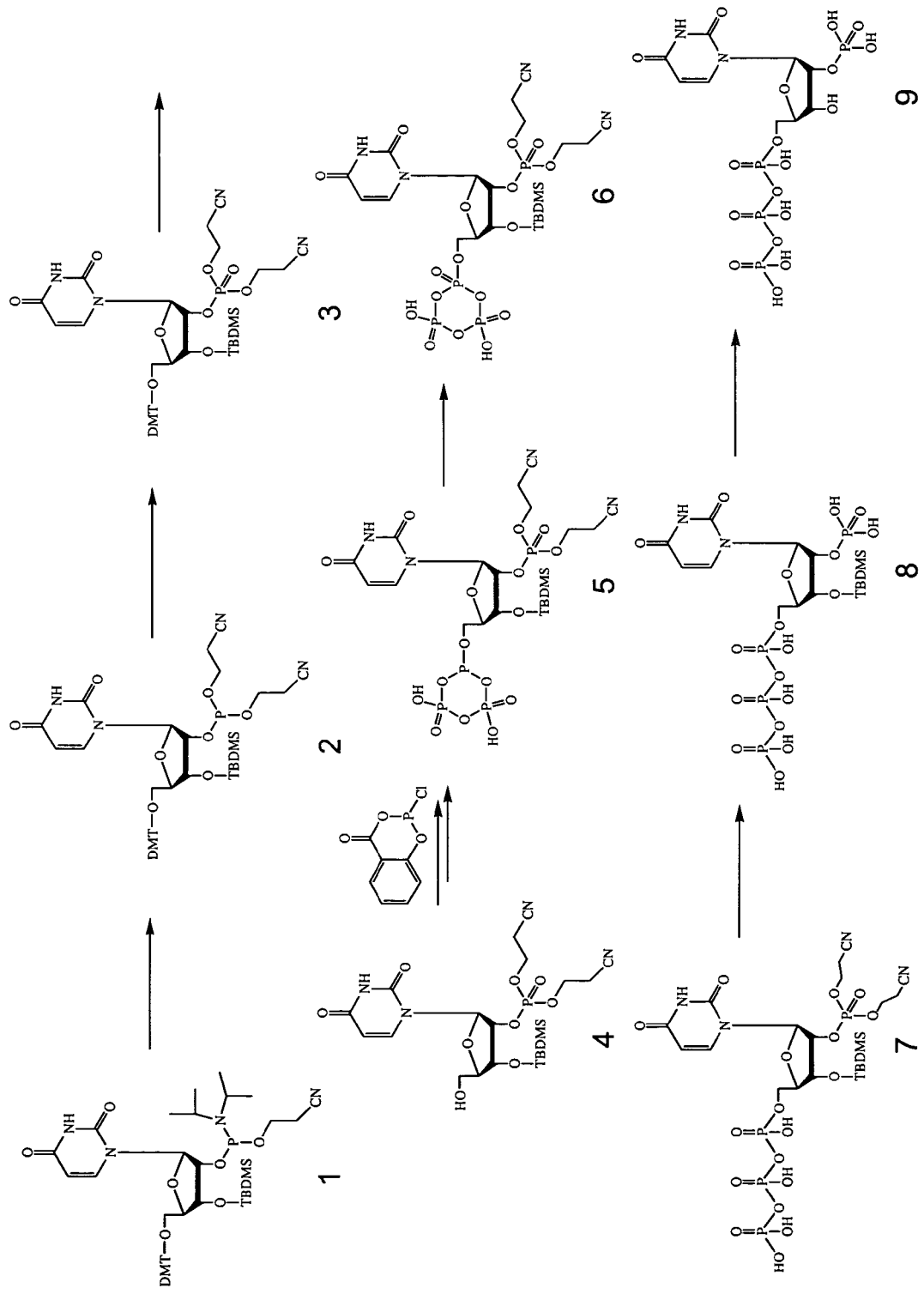
FIG. 12 schematically depicts a regiospecific synthesis pathway for uridine tetraphosphate according to one embodiment of the invention.

FIG. 12 schematically depicts a regiospecific synthesis pathway for uridine tetraphosphate according to one embodiment of the invention. Note that bracketed numbers refer to compounds shown in FIG. 12 in this example.

Synthesis of 5'-O-DMT-3'-O-TBDMS Uridine 2'-O-(biscyanoethyl) Phosphite [2]:

Compound [1] (ChemGenes cat. #ANP-4845, 0.680 g, 0.790 mmol) was taken up in acetonitrile (Aldrich, anhydrous, 10 mL). 1-H-Tetrazole (Aldrich, 0.211 g, 3.01 mmol) was added to the solution in one portion followed by 3-hydroxypropionitrile (Aldrich, 0.109 mL, 1.58 mmol). The resulting solution was stirred at ambient temperature under an atmosphere of argon for 1 hour. The solvent was removed on a rotary evaporator. The residue was taken up in EtOAc (50 mL), and the resulting solution was washed with saturated aqueous $NaHCO_3$ (2×20 mL). The organic layer was separated and was dried over $MgSO_4$. The crude product was obtained by filtration followed by evaporation of the solvent. A Biotage flash 40S cartridge was preconditioned by eluting a solution of 2% $Et_3N$ in $CH_2Cl_2$ (200 mL) prior to loading the product mixture. The product mixture was loaded onto the top of the Biotage column as a solution in a minimum amount of $CH_2Cl_2$. The product was purified by eluting with a stepped gradient which consisted of 2% $Et_3N$/98% $CH_2Cl_2$ (200 mL), 0.5% methanol/2% $Et_3N$/97.5% $CH_2Cl_2$ (200 mL), 1% methanol/2% $Et_3N$/97% $CH_2Cl_2$ (200 mL). The purified product eluted in the 0.5-1.0% methanol solvent strength fractions. The fractions which contained the purified product were combined, and the solvent was removed on a rotary evaporator. The purified product [2] was obtained in this manner as a white foam (0.510 g, 78% yield).

Synthesis of 5'-OH-3'-O-TBDMS Uridine 2'-O-(biscyanoethyl) Phosphate [4]:

The compound [2] (0.335 g, 0.403 mmol) was dissolved in THF (Aldrich, anhydrous, 6.7 mL) at room temperature. A solution of 12 in pyridine/THF/$H_2O$ (0.02M, 2.2:6.8:1; Glen Research, 24 mL, 0.48 mmol) was added to the mixture with stirring. The resulting solution was allowed to stir for 20 minutes at ambient temperature. An aqueous solution of sodium hydrogen sulfite (1 g in 3 mL $H_2O$) was added dropwise until the $I_2$ color was quenched in the solution. The volatile solvents were removed on a rotary evaporator. The solution was diluted to a total volume of 100 mL with EtOAc. The solution was washed carefully with saturated aqueous $NaHCO_3$ (50 mL). The organic layer was separated and dried over $MgSO_4$. The solution was filtered, and the solvent was removed on a rotary evaporator to give compound [3]. This crude [3] material was taken up in $CH_2Cl_2$ (8 mL) with stirring. The resulting solution was cooled to −30° C. A solution of trichloroacetic acid (Fisher, 0.487 g, 2.98 mmol) in $CH_2Cl_2$ (4 mL) was added to the cooled stirring solution of nucleoside. The red/brown color characteristic of the trityl cation appeared immediately. Stirring was continued at −30° C. for 20 minutes after the addition of trichloroacetic acid. MeOH (1.5 mL) was added and the resulting solution was transferred to a separatory funnel. The solution was diluted with $CH_2Cl_2$ (75 mL). The resulting solution was washed with saturated aqueous NaHCO$_3$ (2×30 mL). The organic layer was separated and was dried over Na$_2$SO$_4$. The solution was filtered, and the solvent was removed on a rotary evaporator. The crude product was purified by flash column chromatography on silica gel using a Biotage 40S cartridge. The product was loaded onto the top of the Biotage column as a solution in a minimum amount of CH$_2$Cl$_2$. The product was eluted using a stepped gradient of EtOAc (200 mL), 1% MeOH in EtOAc (200 mL), 2% MeOH in EtOAc (200 mL), 3% MeOH in EtOAc (200 mL), 4% MeOH in EtOAc (200 mL), 5% MeOH in EtOAc (200 mL) and 10% MeOH in EtOAc (200 mL). The product eluted using the 10% MeOH solvent strength. The fractions containing the purified product were combined, and the solvent was removed on a rotary evaporator. The pure product [4] was obtained in this manner as a white foam (0.145 g, 66% yield).

Conversion of Compound [4] to its Corresponding Triphosphate [7]:

5'-OH-3'-O-TBDMS Uridine 2'-O-(biscyanoethyl) phosphate (compound [4], 0.0335 g, 0.0615 mmol) was dried by co-evaporation with pyridine (3×0.2 mL). The resulting material was taken up in pyridine (Aldrich, anhydrous, 70 µL) and DMF (Aldrich, anhydrous, 180 µL). A solution of salicylphosphorochloridite in DMF (0.5 M, 137 µL, 0.0677 mmol) was added to the stirring solution. The resulting reaction mixture was stirred at ambient temperature for 20 minutes. Tri-N-butylamine (Aldrich, 38 µL, 0.160 mmol) was added, followed by a solution of tetrabutylammonium pyrophosphate in DMF (0.5 M, 185 µL, 0.0925 mmol). The resulting reaction mixture was stirred at ambient temperature for 20 minutes. A solution of 12 in pyridine/H$_2$O/THF (0.02 M, Glen Research, 3.6 mL, 0.072 mmol) was added, and the resulting reaction mixture was stirred for a further 20 minutes at ambient temperature. The excess iodine was quenched by dropwise addition of a sodium hydrogen sulfite solution (1 g of NaHSO$_3$ in 3 mL of water) until the characteristic color of the iodine had disappeared. The resulting solution was allowed to stand at ambient temperature overnight. Note that standing at −20° C. over 72 hours accomplishes the same transformation of cyclic triphosphate to linear triphosphate. At this point, no cyclic triphosphate was detectable by flow injection mass spectrometry (MS). The resulting linear triphosphate was isolated by reversed phase HPLC (Column: Zorbax SB-C18, 21.2 mm×25 cm. Solvent A: 0.1 M TEAA, 2.5% CH$_3$CN, pH=7.0; Solvent B: CH$_3$CN. Flow rate: 10.0 ml/minute. Gradient: t=0 minutes, 100% A; t=15 minutes, 50% A/50% B; t=20 minutes, 100% B; t=25 minutes, 100% B; t=25.01 minutes, 100% A; t=30-minutes, 100% A. Retention time: 20.9 min.).

Synthesis of 3'-O-TBDMS-Uridine Tetraphosphate [8]:

The uridine 2'-O-bis(O-cyanoethyl) phosphate [7] (9 mg, 0.0117 mmol) was coevaporated successively with MeOH (3×5 mL), CH$_2$Cl$_2$ (3×5 mL) and finally with anhydrous CH$_3$CN (1×5 mL). The material was then taken up in CH$_3$CN (Aldrich, anhydrous, 2.25 mL). 1,8-Diazabicyclo[5.4.0]undec-7-ene (DBU, Aldrich, 175 µL, 1.17 mmol) and chlorotrimethylsilane (Aldrich, 59 µL, 0.468 mmol) were added to the stirring solution. The reaction mixture was allowed to stir at ambient temperature for 2 hours. Water (1 mL) was added, and the volatile materials were removed by a rotary evaporator. The resulting product was purified by reversed phase HPLC. (Column: Zorbax SB-C18, 21.2 mm×25 cm. Solvent A: 0.1 M TEAA, 2.5% CH$_3$CN, pH=7.0; Solvent B: CH$_3$CN. Flow rate: 10.0 mL/minute. Gradient: t=0 minutes, 100% A; t=15 minutes, 50% A/50% B; t=20 minutes, 100% B; t=25 minutes, 100% B; t=25.01 minutes, 100% A; t=30 minutes, 100% A. Retention time: 13.6 minutes). The compound [8] obtained in this manner after lyophilization was quantified by UV (8 mg). The molar extinction co-efficient ($\epsilon_{max}$) of uridine was taken to be 10(mM$^{-1}$ cm$^{-1}$) and its absorption maxima ($\lambda_{max}$) was taken to be 262 nm.

Synthesis of Uridine Tetraphosphate [9]:

The 3'-O-TBDMS-Uridine Tetraphosphate [8] (2.55 mg, 0.00376 mmol) was taken up in CH$_3$CN (Aldrich anhydrous, 160 µL). Tetrabutylammonium fluoride in THF (1.0 M, Aldrich, 113 µL, 0.113 mmol) and HOAc (glacial, Aldrich, 2.2 µL, 0.0376 mmol) were added to the solution. The resulting reaction mixture was allowed to stir for 21 hours at ambient temperature. HPLC analysis of the reaction at this time showed no remaining silyl ether. The volatile materials were removed on a rotary evaporator. The product mixture was resuspended in H$_2$O, and the product was purified by reversed phase HPLC. (Column: Zorbax SB-C18, 9.4 mm×25 cm. Solvent A: 0.1 M TEAA, 2.5% CH$_3$CN, pH=7.0; Solvent B: CH$_3$CN. Flow rate: 4.0 mL/minute. Gradient: t=0 minutes, 100% A; t=15 minutes, 75% A/25% B; t=15.01 minutes, 100% B; t=20 minutes, 100% A; t=27 minutes, 100% A. Retention time: 7.05 minutes). The purified material was lyophilized. The resulting material was resuspended and lyophilized a total of 5 times to ensure complete removal of TEAA salts. Before the final lyophilization, the material was quantified by UV (2.00 mg, 94% yield). The compound [9] obtained in this manner was a white solid.

Example II

Synthesis of Adenosine Tetraphosphate

Overview

This example illustrates the synthesis of adenosine tetraphosphate according to one synthetic reaction of the present invention. As schematically shown, in FIG. 13 the synthetic reaction produced a mixture of 5'-triphosphate-3'-monophosphate adenine nucleosides and 5'-triphosphate-2'-monophosphate adenine nucleosides. In the synthetic reaction, ATP was reacted with trisodium trimetaphosphate (NaPO$_3$)$_3$ in 1N KOH at room temperature. The reaction mixture was allowed to proceed for 8 hours. The molar ratio of 5'-triphosphate-3'-monophosphate adenine nucleoside to 5'-triphosphate-2'-monophosphate adenine nucleoside produced was approximately 50:50.

Figure 14A:
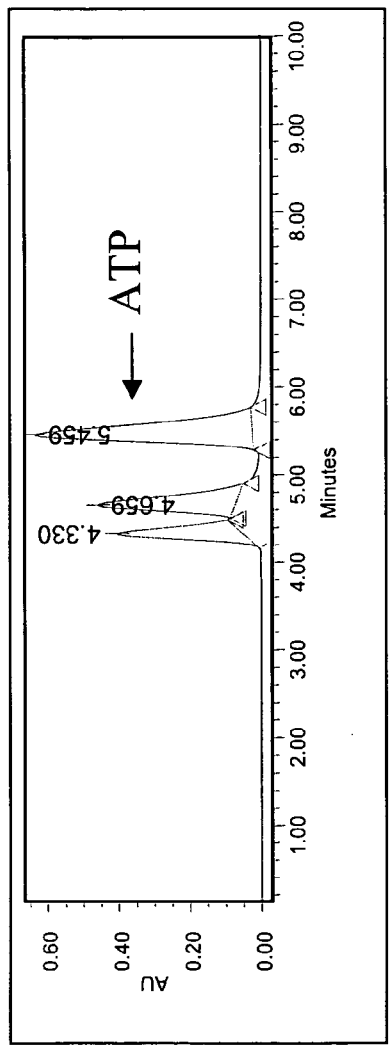
FIGS. 14A-C are HPLC traces that show the detection of adenosine tetraphosphate nucleotides of the invention.
Figure 14B:
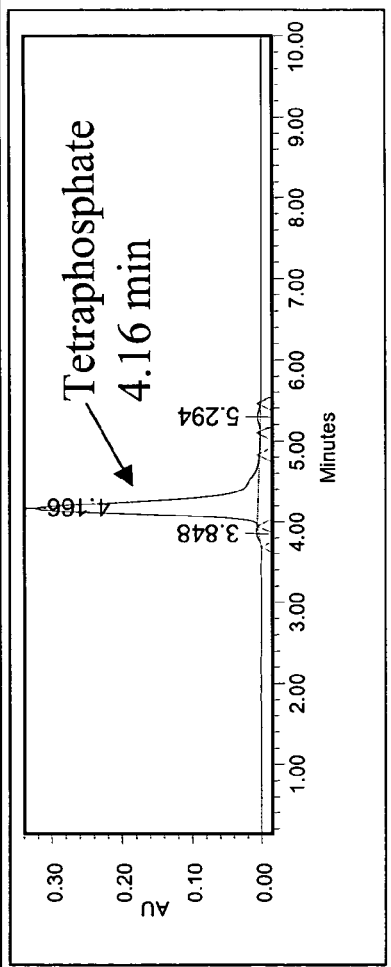
Figure 14C:
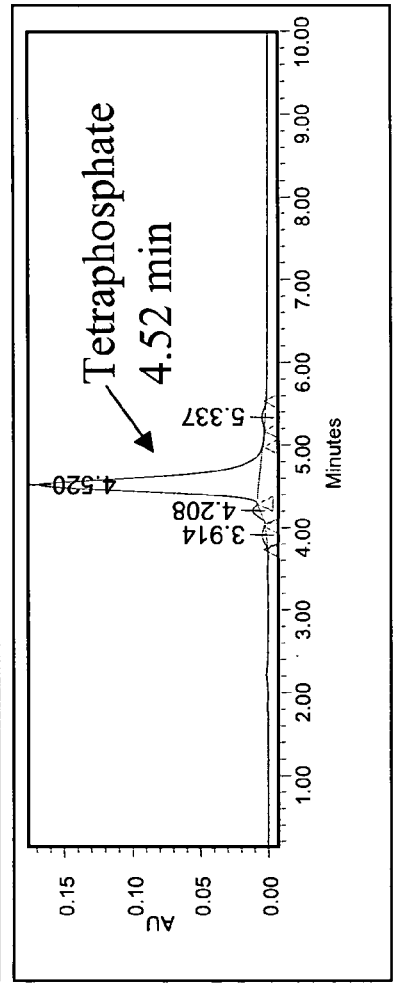

FIGS. 14A-C are HPLC traces (abscissa—retention time (minutes); ordinate—absorbance units (AU) at 260 nm) showing the detection of various adenosine nucleotides. The traces were generated following nucleotide separation using ion-pairing RP-HPLC chromatography. In particular, the analysis and purification was carried out on Symmetry-Shield™ reverse phase column (Waters Corporation, Milford, Mass.) with TEAA-acetonitrile buffer. FIG. 14A shows the HPLC analysis of the adenosine tetraphosphate reaction, whereas FIGS. 14B and C show the HPLC analysis of purified adenosine tetraphosphate fractions (retention times: 4.166 and 4.52 minutes, respectively). A separate NMR analysis ($^{31}$P NMR; 2D Proton-Phosphorus NMR), which is described further below, revealed that the peak that eluted at 4.33 minutes corresponds to 2'-PO$_4$-ATP and the peak at 4.65 minutes corresponds to 3'-PO$_4$-ATP (see, FIG. 14A).

NMR Analysis

The $^1$H and $^{31}$P chemical shifts of the adenosine tetraphosphate with the peak at 4.33 minutes in the HPLC analysis, described above, are shown in Table I. The assignment of the proton chemical shifts was facilitated by the COSY spectrum and the fact that proton H-1' could easily be identified because it should have had only one proton coupling and it should have been the furthest downfield of the ribose protons.

TABLE I

| Atom | $^1$H Shift (ppm), Multiplicity, Splittings | $^{31}$P Shift (ppm), Multiplicity, P—P Splittings |
|---|---|---|
| 2 | 8.50, s | — |
| 8 | 8.27, s | — |
| 1' | 6.27, d, 5.4 Hz | — |
| 2' | 5.05, d of t, 8.8, 5.5 Hz | — |
| 3' | 4.67, d of d, 5.4, 4.1 Hz | — |
| 4' | 4.41, m | — |
| 5' | 4.26, d of d, 5.2, 3.3 Hz | — |
| P2' | — | 0.87, s |
| Pα | — | −10.69, d, 19.5 Hz |
| Pβ | — | −22.44, t, 19.5 Hz |
| Pγ | — | −9.92, d, 19.5 Hz |

$^{31}$P spectra with and without proton decoupling were also acquired. Four phosphate peaks were observed in the $^{31}$P spectra. Three of the peaks at −22.44, −10.69, and −9.92 ppm showed $^{31}$P-$^{31}$P coupling and belonged to the triphosphate group at the 5' position of the ribose ring. The fourth peak, at 0.87 ppm, showed no $^{31}$P-$^{31}$P coupling and belonged to the monophosphate. However, the $^{31}$P chemical shift of the monophosphate was very similar in both adenosine tetraphosphates (i.e., peaks at 4.33 and 4.65 minutes), 0.87 and 1.08 ppm respectively, and therefore was not useful in determining the position of the phosphate group. Additionally, the linewidths of the monophosphate and triphosphate peaks were so broad that the $^{31}$P-$^1$H couplings were not resolved in the $^{31}$P spectrum acquired without proton decoupling.

Figure 13:
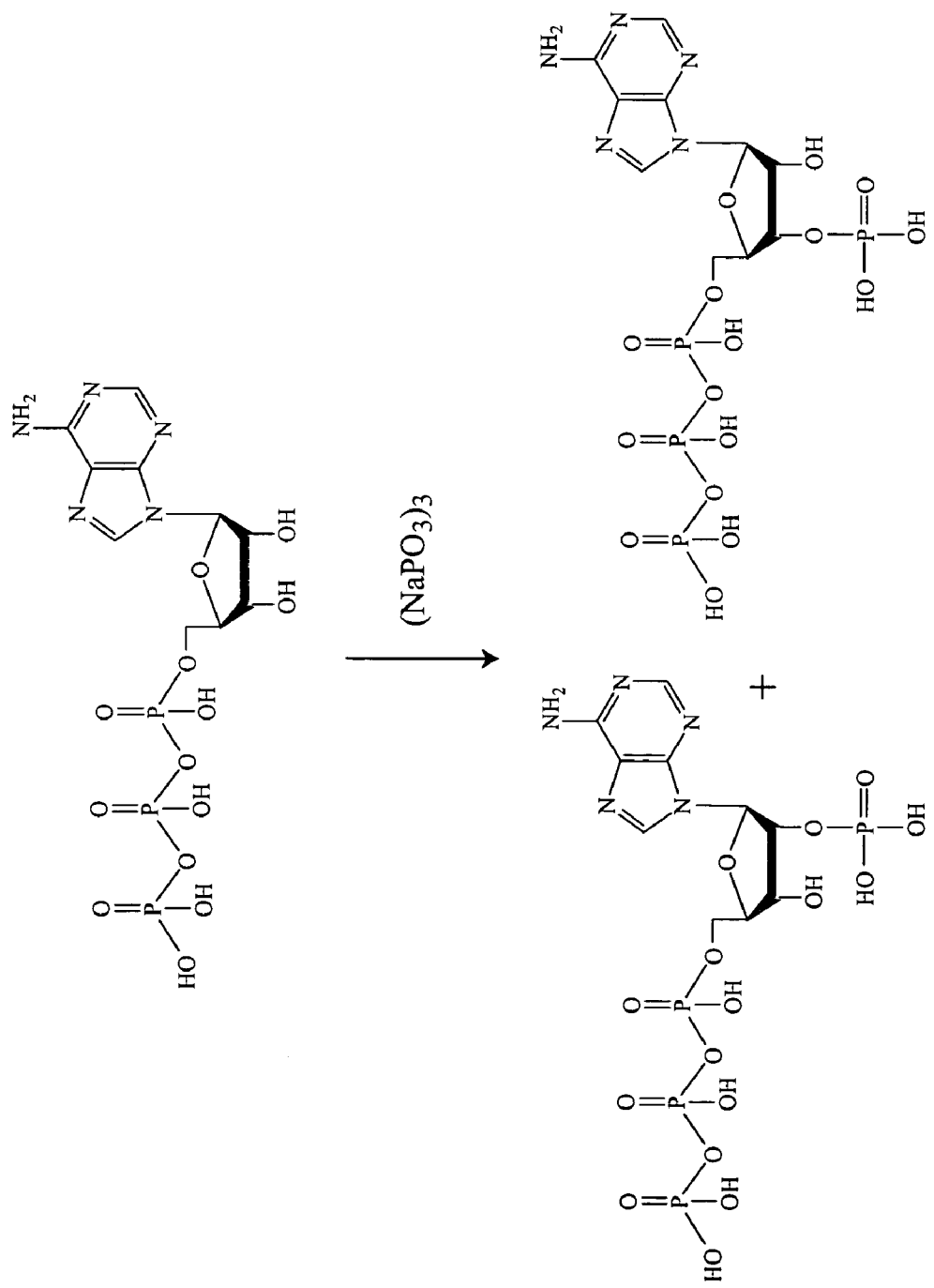
FIG. 13 schematically illustrates a synthetic reaction that produces a mixture of 5'-triphosphate-3'-monophosphate adenine nucleosides and 5'-triphosphate-2'-monophosphate adenine nucleosides according to one embodiment of the invention.

A comparison of the H-2' and H-3' chemical shifts of adenosine 5'-phosphate, adenosine 2'-monophosphate, and adenosine tetraphosphate (peak at 4.33 minutes) showed that the mono-phosphate is attached at C-2' of the adenosine tetraphosphate with a peak at 4.33 minutes (see, Table II). Additionally, H-2', which had two neighboring protons and therefore was expected to be a doublet of doublets or a triplet, was a doublet of triplets. The additional 8.8 Hz coupling is the right magnitude to be a three bond $^{31}$P-$^1$H coupling. Based upon these results, the structure of the adenosine tetraphosphate with a peak at 4.33 minutes was determined and corresponds to 2'-PO$_4$-ATP. The structure of 2'-PO$_4$-ATP is schematically shown in FIG. 13.

TABLE II

| Molecule | H-2' (ppm) | H-3' (ppm) |
|---|---|---|
| Adenosine 5'-phosphate | 4.75 | 4.51 |
| Adenosine 2'-monophosphate | 5.19 | 4.57 |
| Adenosine tetraphosphate (4.33 minutes) | 5.05 | 4.67 |

The sample with a peak at 4.65 minutes was a mixture of a nucleotide and what appeared to be a large amount of triethylamine salt. The $^1$H and $^{31}$P chemical shifts and measured splittings of the nucleotide, as measured from the $^1$H and $^{31}$P spectra, are shown in Table III. Like the adenosine tetraphosphate with a peak at 4.33 minutes, the assignment of the proton chemical shifts was facilitated by the COSY spectrum and the fact that proton H-1' could easily be identified because it should have had only one proton coupling and it should have been the furthest downfield of the ribose protons. The coupled and decoupled $^{31}$P spectra were not useful for the same reasons discussed above for the adenosine tetraphosphate having a peak at 4.33 minutes.

TABLE III

| Atom | $^1$H Shift (ppm), Multiplicity, Splittings | $^{31}$P Shift (ppm), Multiplicity, P—P Splittings |
|---|---|---|
| 2 | 8.56, s | — |
| 8 | 8.27, s | — |
| 1' | 6.18, d 6.7 Hz | — |
| 2' | ~4.8, m | — |
| 3' | ~4.8, m | — |
| 4' | 4.60, p, ~2.8 | — |
| 5$_a$' | 4.28, d of d of d, 12.0, 5.2, 2.8 | — |
| 5$_b$' | 4.23, d of d of d, 12.0, 4.4, 2.6 | — |
| P3' | — | 1.08, s |
| Pα | — | −10.70, d, 19.0 Hz |
| Pβ | — | −22.42, t, 19.0 Hz |
| Pγ | — | −9.92, d, 19.0 Hz |

The chemical shifts of H-2' and H-3' were both about 4.8 ppm for the adenosine tetraphosphate sample with the peak at 4.65 minutes. H-2', therefore, moved back upfield, close to the chemical shift of H-2' in adenosine 5'-phosphate, 4.75 ppm (see, Table II). H-3' moved downfield relative to the chemical shift of H-3' in both adenosine 5'-phosphate, 4.51 ppm, and adenosine tetraphosphate (peak at 4.33 minutes), 4.67 ppm (see, Table II). Based on these observations, the structure of the adenosine tetraphosphate with a peak at 4.65 minutes was determined and corresponds to 3'-PO$_4$-ATP. The structure of 3'-PO$_4$-ATP is schematically shown in FIG. 13.

Example III

Figure 15:
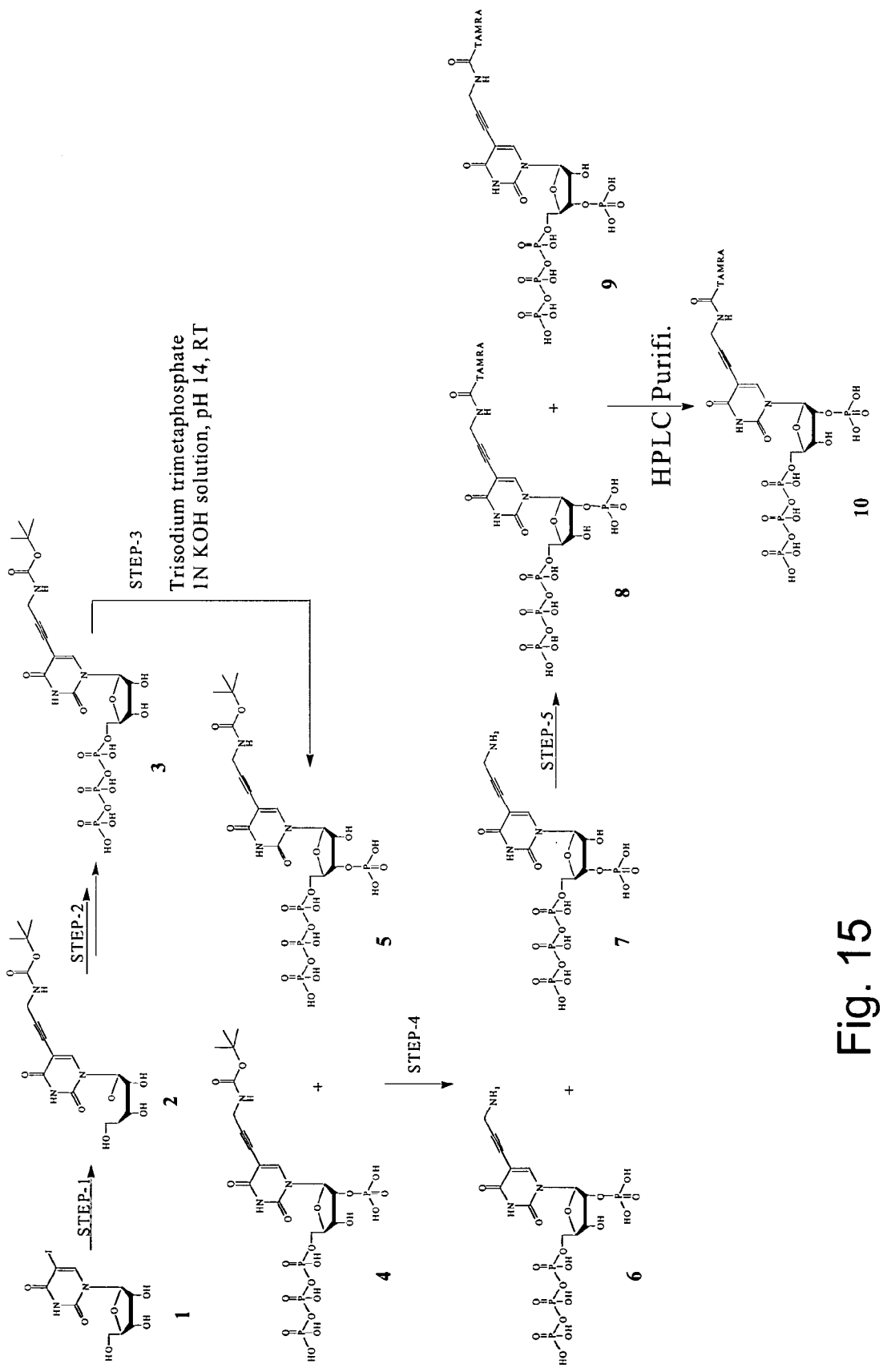
FIG. 15 schematically shows certain steps in a synthesis pathway for TAMRA labeled uridine tetraphosphates according to one embodiment of the invention.

Synthesis of TAMRA Labeled 2'-Monophosphate-Uridine Triphosphates and 3'-Monophosphate-Uridine Triphosphates This example illustrates a synthetic pathway for TAMRA labeled 2'-monophosphate-uridine triphosphates and 3'-monophosphate-uridine triphosphates according to one embodiment of the invention. To further illustrate, FIG. 15 schematically shows certain steps in the pathway that are described in this example. Note that bracketed numbers refer to compounds shown in FIG. 15 in this example.

Figure 16:
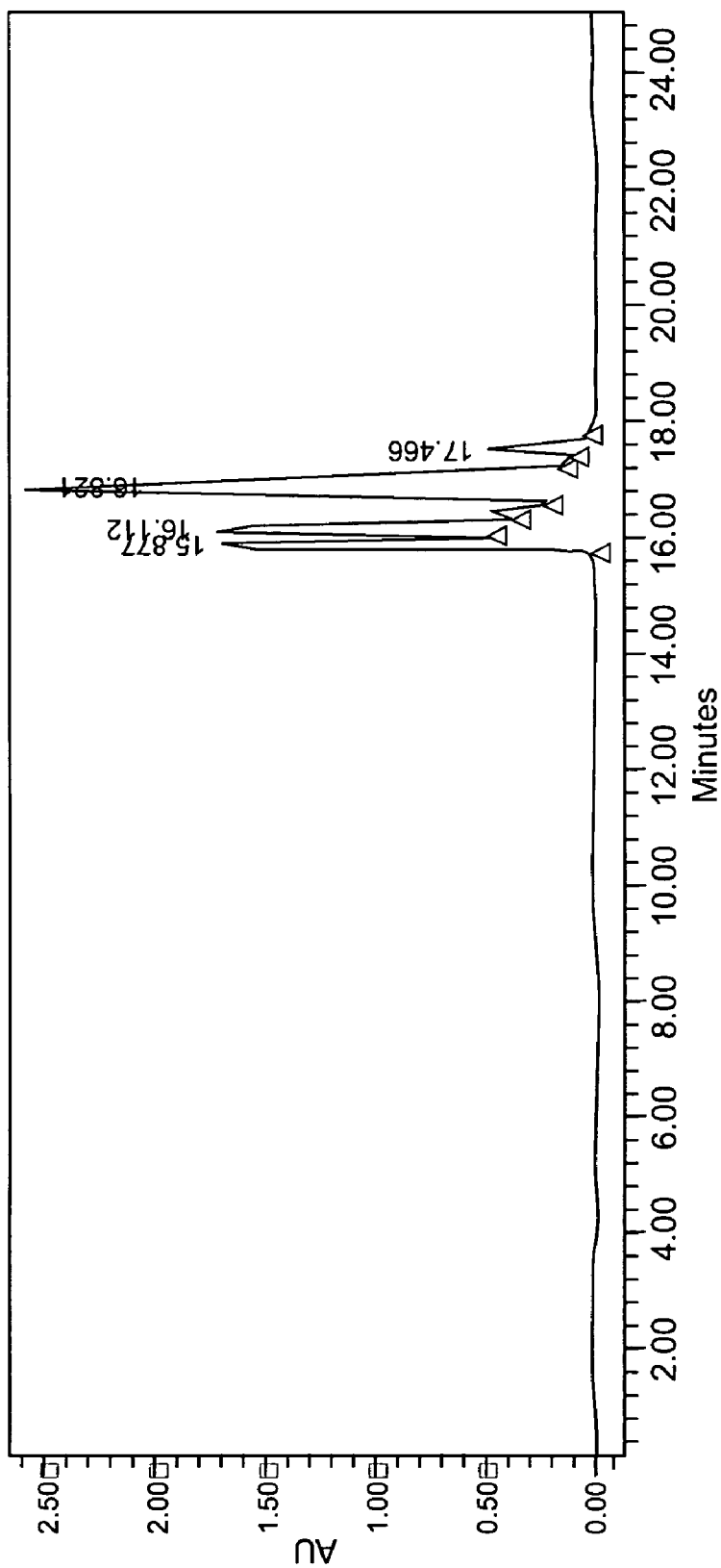
FIG. 16 is an HPLC chromatogram that shows the detection of BOC-protected propargyl uridine tetraphosphates corresponding to structures 5 and 6 shown in FIG. 15.

Compound [3] was taken up in H$_2$O (300 µL) and 100 µL of this solution was added to a conical vial. The solution in the conical vial was diluted with 1.0 mL of 1N KOH. Sodium trimetaphosphate (50 mg) was added and the solution was stirred at ambient temperature for one hour. Fifty mg of sodium trimetaphosphate was added and stirring was continued for two additional hours. An additional 50 mg of sodium trimetaphosphate was then added and stirring was continued overnight at ambient temperature. The next day, 80 µL of glacial acetic acid was added to bring the pH to about 7.0. The resulting reaction mixture was then purified by RP-HPLC. First, the portion of the reaction mixture including the nucleoside was separated from the salts. After lyophilization, the tetraphosphates were separated from the starting material. FIG. 16 is a chromatogram (abscissa—retention time (minutes); ordinate—absorbance units (AU) at 290 nm) that shows the detection of these tetraphosphates. In particular, the peaks eluted at 15.9 and 16.1 minutes correspond to the tetraphosphates and the peak at 16.8 corresponds to the starting material.

Seven mg of the tetraphosphate isomer mixture (compounds [4] and [5]) were taken up in 200 µL of trifluoroacetic acid (TFA) at ambient temperature. The resulting solution was stirred for 30 minutes. The solution was then cooled in liquid nitrogen and the TFA was removed with lyophilization. The material was carried on to reaction with carboxytetramethylrhodamine succinimidyl ester (TAMRA-SE) without further manipulation.

A TAMRA-SE stock solution was prepared by dissolving 5 mg of TAMRA-SE in 350 μL of dimethylformamide (DMF). In addition, a tetraphosphate stock solution (including compounds [6] and [7]) was prepared by dissolving 6 mg of the tetraphosphate mixture in 100 μL of $H_2O$.

The TAMA-SE stock solution was transferred to a conical vial along with 175 μL of $H_2O$. In addition, 1.875 μL of a labeling buffer (0.1M sodium tetraborate) and the tetraphosphate stock solution was added to the mixture. The resulting reaction mixture was stirred in the dark (conical vial covered with aluminum foil) at ambient temperature overnight. The next day, HPLC separation of 100 μL of the reaction mixture showed two peaks eluting at approximately 17 minutes, which were thought to be the labeled tetraphosphate isomers (compounds [8] and [9]). Fractions corresponding to these peaks were isolated from the rest of the reaction mixture by RP-HPLC. After concentrating the collected sample by lyophilization, flow injection analysis-mass spectrometry (FIA-MS) showed an ion at 1027.8, which deviated from the mass of the expected (M-H)⁻ ion by one mass unit. The remainder of the reaction mixture was allowed to stir at ambient temperature overnight.

It is believed that since the fluorescent label is positively charged, the removal of one proton (M-H) would yield an overall neutral molecule. Therefore, (M-2H) would lead to a molecule detectable by MS as a mass:charge ratio of −1. This may account for the observed molecular ion referred to above.

Figure 17:
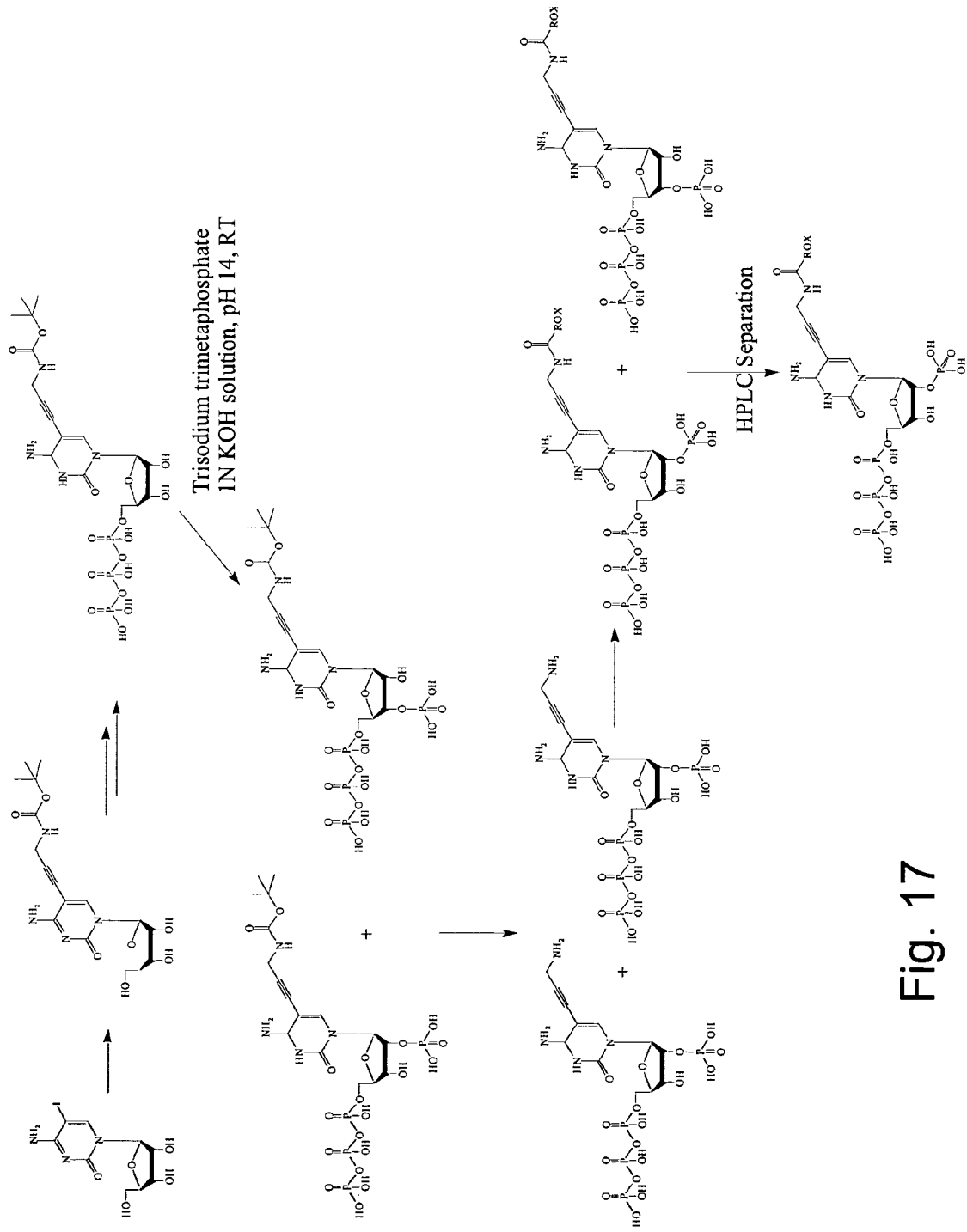
FIG. 17 schematically illustrates certain steps in a synthesis pathway for ROX labeled cytidine tetraphosphates according to one embodiment of the invention.
Figure 18:
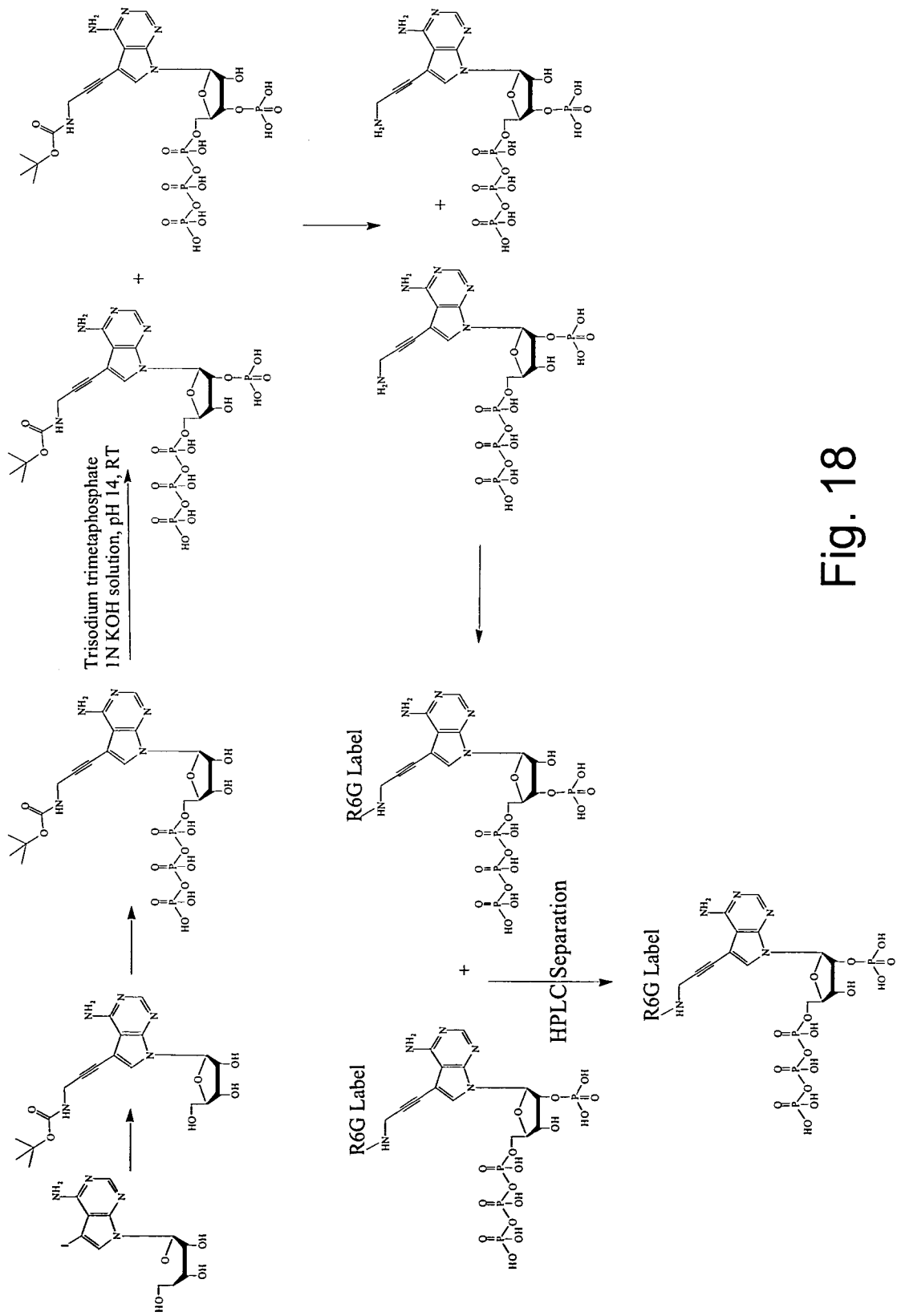
FIG. 18 schematically depicts certain steps in a synthesis pathway for R6G labeled adenine tetraphosphates according to one embodiment of the invention.
Figure 19:
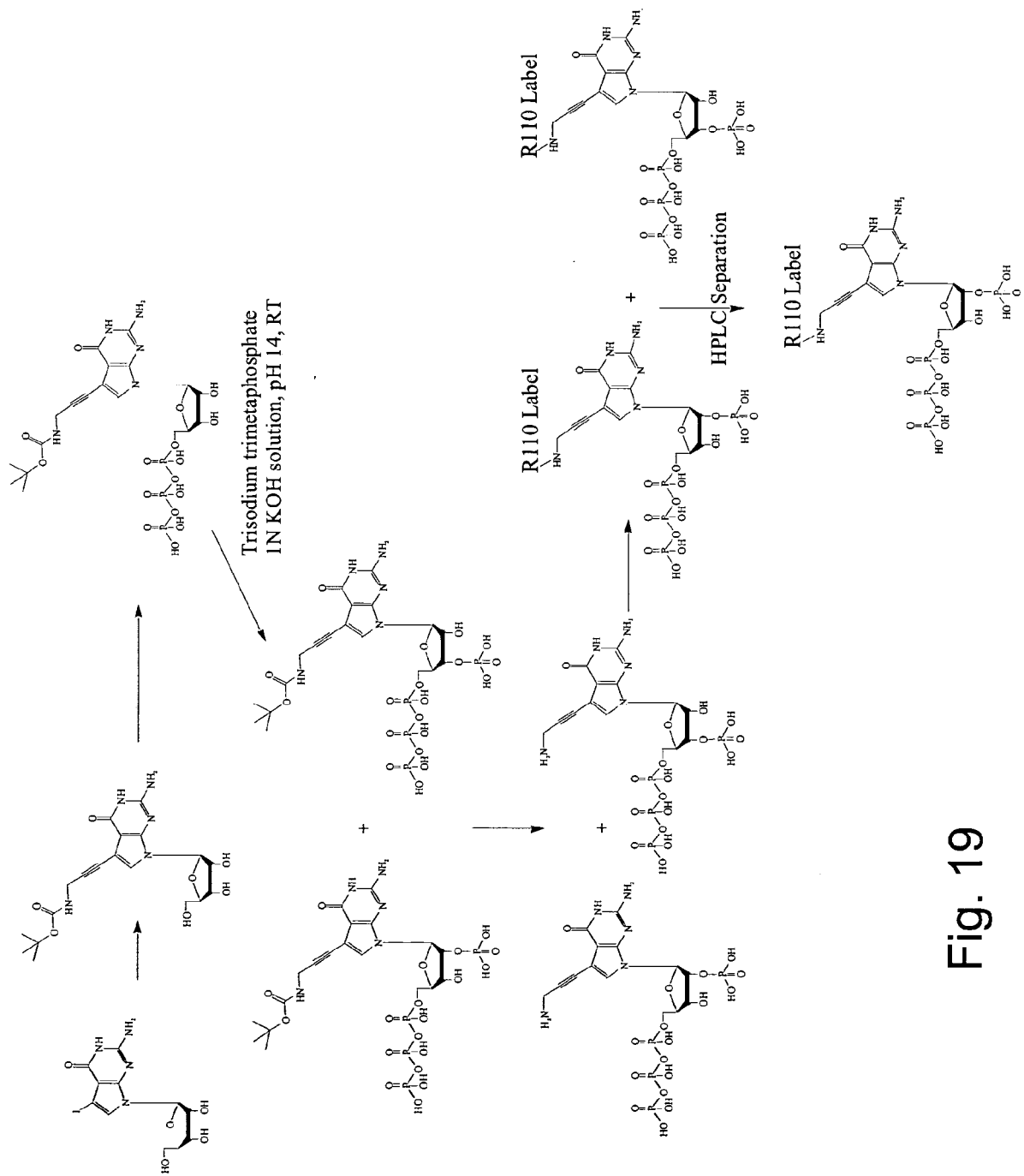
FIG. 19 schematically shows certain steps in a synthesis pathway for R110 labeled guanine tetraphosphates according to one embodiment of the invention.

Other exemplary synthesis pathways for additional labeled tetraphosphates are schematically depicted in FIGS. 17-19. In particular, FIG. 17 schematically illustrates certain steps in a synthesis pathway for ROX labeled cytidine tetraphosphates. FIG. 18 schematically depicts certain steps in a synthesis pathway for R6G labeled adenine tetraphosphates. FIG. 19 schematically shows certain steps in a synthesis pathway for R110 labeled guanine tetraphosphates.

Example IV

Termination of Primer Nucleic Acid Extension Using 2'-Terminator Nucleotides

Figures 20A, 20B, 20C, 20D:
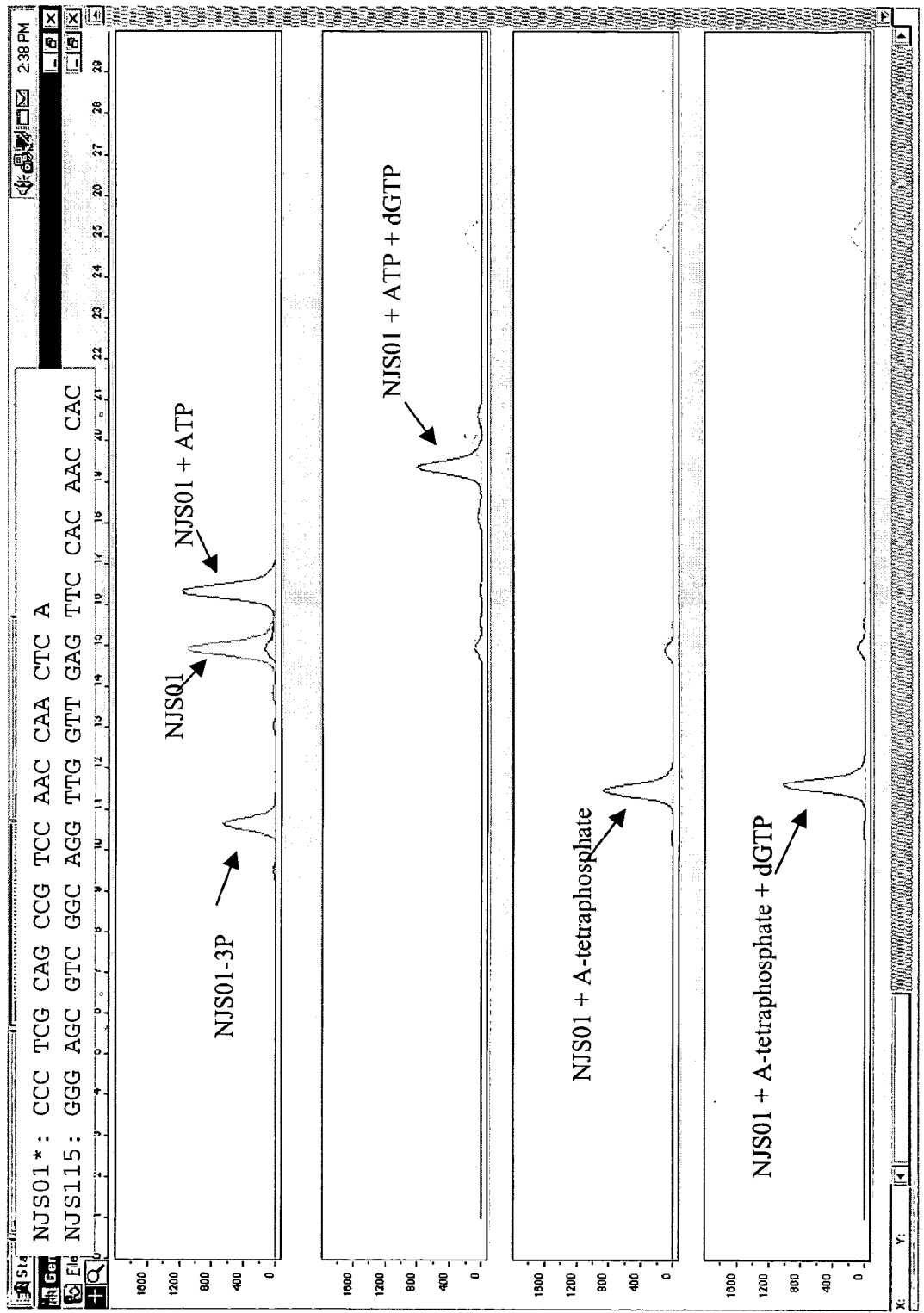
FIGS. 20A-D are electropherograms that show the detection of various extended primer nucleic acids.

This example shows a comparison of two primer nucleic acid extension reactions. The sequences of the template and primer nucleic acids used in these analyses are shown in FIG. 20, corresponding to sequence designations NJS115 and NJS01*, respectively. FIGS. 20A and B are electropherogram traces that show the incorporation of adenine and guanine residues into NJS01* in a reaction that did not involve terminator nucleotides. In contrast, FIGS. 20C and D are electrophoretogram traces that show that NJS01* is rendered non-extendible upon the incorporation of an adenosine tetraphosphate terminator nucleotide of the invention.

Example V

Automated Cycle DNA Sequencing Using a Modified Thermostable DNA Polymerase and Fluorescent Primers This example illustrates the application of the 2'-terminator nucleotides of the invention to automated dye primer cycle DNA sequencing. In particular, an M13mp18 DNA template was sequenced using ribonucleoside 2'-monophosphate 5'-triphosphates.

Cycle sequencing reactions were performed with G46E E678G CS5 DNA polymerase (referred to above) modified for the incorporation of ribonucleotide analogs, dye primers, and ribonucleoside 2'-monophosphate 5'-triphosphate analogs. Reactions consisted of 50 mM Tricine pH 8.5; 40 mM KOAc; 4 mM Mg(OAc)₂; 100 μM each dATP, dCTP, dTTP; 150 μM c7dGTP; 0.5 unit/μl G46E E678G CS5 DNA polymerase; 1.0 unit/μl rTth Thermostable Pyrophosphatase; and 20 ng/μl M13mp18 template. Four individual reactions, one for each base were performed. Reactions for each of the bases contained the above plus the following reagents:

| | |
|---|---|
| Adenosine reactions (10 μl): | |
| 3.5 μM | Adenosine 2'-monophosphate 5'-triphosphate |
| 0.1 μM | FR686NHEX primer |
| Cytidine reactions (10 μl): | |
| 7.5 μM | Cytidine 2'-monophosphate 5'-triphosphate |
| 0.1 μM | FR686NFAM primer |
| Guanosine reactions (20 μl): | |
| 5 μM | Guanosine 2'-monophosphate 5'-triphosphate |
| 0.1 μM | FR686NTAMRA primer |
| Uridine reactions (20 μl): | |
| 10 μM | Uridine 2'-monophosphate 5'-triphosphate |
| 0.1 μM | FR686NROX primer |

In the adenosine reactions, the adenosine 2'-monophosphate 5'-triphosphate was approximately 95% pure (i.e., about 5% was the adenosine 3'-monophosphate 5'-triphosphate). In the cytidine reactions, the cytidine 2'-monophosphate 5'-triphosphate and the cytidine 3'-monophosphate 5'-triphosphate were present as 50/50 mixture. In the guanosine reactions, the guanosine 2'-monophosphate 5'-triphosphate was approximately 94% pure (i.e., about 6% was the guanosine 3'-monophosphate 5'-triphosphate). In the uridine reactions, the uridine 2'-monophosphate 5'-triphosphate was 100% pure.

The oligonucleotide primer sequences were, as follows (primer FR686N is SEQ ID NO:1):

```
FR686NFAM    GCGCCAGGGTTTTCCCAGTEA
             E = 2'-amino (ribo) C F = 5' FAM ABD
FR686NHEX    ICGCCAGGGTTTTCCCAGTEA
             E = 2'-amino (ribo) C I = 5' HEX ABD
FR686NROX    JCGCCAGGGTTTTCCCAGTEA
             E = 2'-amino (ribo) C J = 6-ROX
FR686NTAMRA  LCGCCAGGGTTTTCCCAGTEA
             E = 2'-amino (ribo) C L = C6-amino TAMRA
```

Each of the four reactions were placed in a Perkin-Elmer GeneAmp® PCR system 9600 thermal cycler and subjected to 95° C. for 45 seconds and then 20 cycles of 95° C. for 15 seconds, 55° C. for 15 seconds, 70° C. for 90 seconds, followed by 20 cycles of 95° C. for 15 seconds, 70° C. for 90 seconds. The four reactions were pooled and precipitated by the addition of 144 μl 100% ethanol and 6 μl 3M NaOAc (pH 5.2) at 4° C. for 15 minutes. The pooled reactions were microcentrifuged at 4° C. for 15 minutes to precipitate the DNA, and the supernatant was removed. The pellet was washed with 350 μl cold 70% ethanol, microcentrifuged at 4° C. for 5 minutes, supernatant removed, and the DNA pellet dried. The precipitated DNA was resuspended in 10 μl Hi-Di formamide (Applied Biosystems, Foster City, Calif., part #4311320), heated at 90° C. for 3 minutes and placed on ice.

2 μL of each sample was loaded onto a pre-electrophoresed 48 cm 4.25% acrylamide:bis (29:1), 6 M urea gel and electrphoresed for 7 hours on an ABI PRISM™ 377 DNA Sequencer (Applied Biosystems, Foster City, Calif.).

Figure 21:
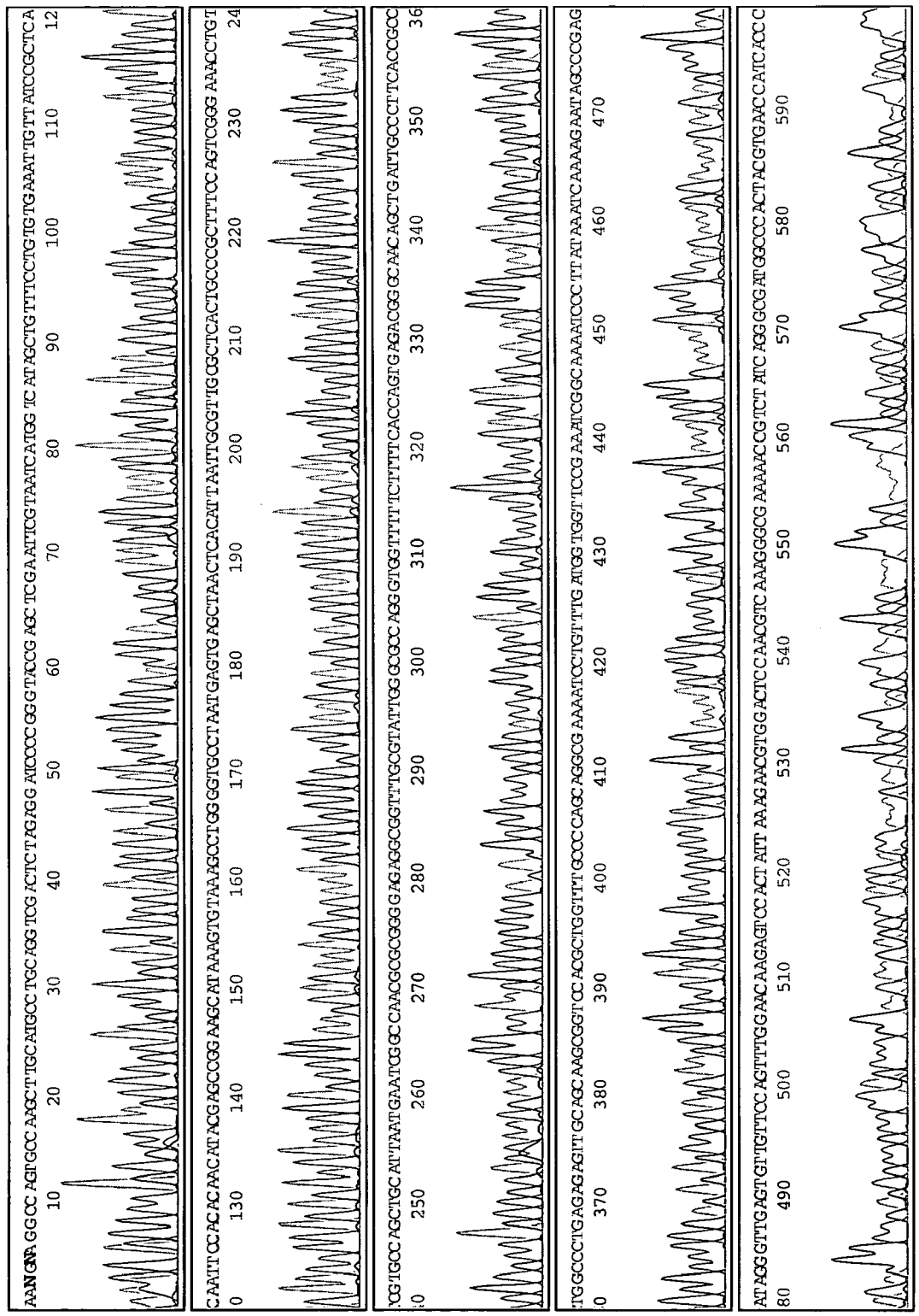
FIG. 21 is a spectral profile that shows the data from a sequence analysis of an M13mp18 DNA template using 2'-terminator nucleotides.

Data was analyzed with Sequencing Analysis Software 3.4.1 (Applied Biosystems, Foster City, Calif.) using primer file DP4% Ac{KS}, the semiadaptive basecaller version 3.3.1b2, and a matrix file specific for the dye primers used above generated following the procedure in the Applied Biosystems manual (part #903436). Automated basecalling by the analysis software was 100% accurate for bases +18 to +739 from the sequencing primer when compared to an M13mp18 reference sequence. FIG. 21 provides a spectral profile of the data from this sequence analysis.

Example VI

Cycled DNA Primer Extension Using a Modified Thermostable DNA Polymerase and Dye-Labeled Ribonucleoside 2'-Monophosphate 5'-Triphosphate A thermal cycled primer extension reaction was performed with G46E E678G CS5 DNA polymerase modified for the incorporation of ribonucleotide analogs, unlabeled primer, and TAMRA dye-labeled uridine 2'-monophosphate 5'-triphosphate. The 20 μl reaction consisted of 50 mM Tricine pH 7.5; 25 mM KOAc; 2.5 mM Mg(OAc)$_2$; 100 μM each dATP, dCTP, and dTTP; 150 μM dTTP; 0.5 unit/μl G46E E678G CS5 DNA polymerase; 1.0 unit/μl rTth Thermostable inorganic pyrophosphatase; 5 ng/μl M13mp18 template; 0.15 μM primer; and 0.25 μM TAMRA-uridine 2'-phosphate 5'-triphosphate.

A control reaction was performed with AmpliTaq DNA polymerase, FS, unlabeled primer and TAMRA dye-labeled ddTTP. The 20 μl reaction consisted of 50 mM Tris pH 9; 2 mM MgCl$_2$; 100 μM each dATP, dCTP, and dTTP; 150 μM dITP; 0.5 unit/μl AmpliTaq DNA polymerase, FS; 1.0 unit/μl rTth Thermostable inorganic pyrophosphatase; 5 ng/μl M13mp18 template; 0.15 μM FR686N primer; and 0.2 μM TAMRA-ddTTP.

```
FR686N    CGCCAGGGTTTTCCCAGTEA    (SEQ ID NO: 1)
          E = 2'-amino (ribo) C
```

The reactions were placed in a Perkin-Elmer GeneAmp® PCR system 9700 thermal cycler and subjected to 96° C. for 20 seconds and then 25 cycles of 96° C. for 10 seconds, 50° C. for 5 seconds, 60° C. for 4 minutes. After cycling unincorporated dye-labeled terminator was removed from the reaction by centrifugation at 700×g for two minutes through a Sephadex-G50 column (Sigma, Part No G-50-80). The sample was heated at 95° C. for 3 minutes and placed on ice. The samples were electrophoresed on an Applied Biosystems 3100 Genetic Analyzer with the GeneScan application following the StdSeq50_POP6DefaultModule parameters using a 50 cm capillary array and POP6 polymer.

Figure 22:
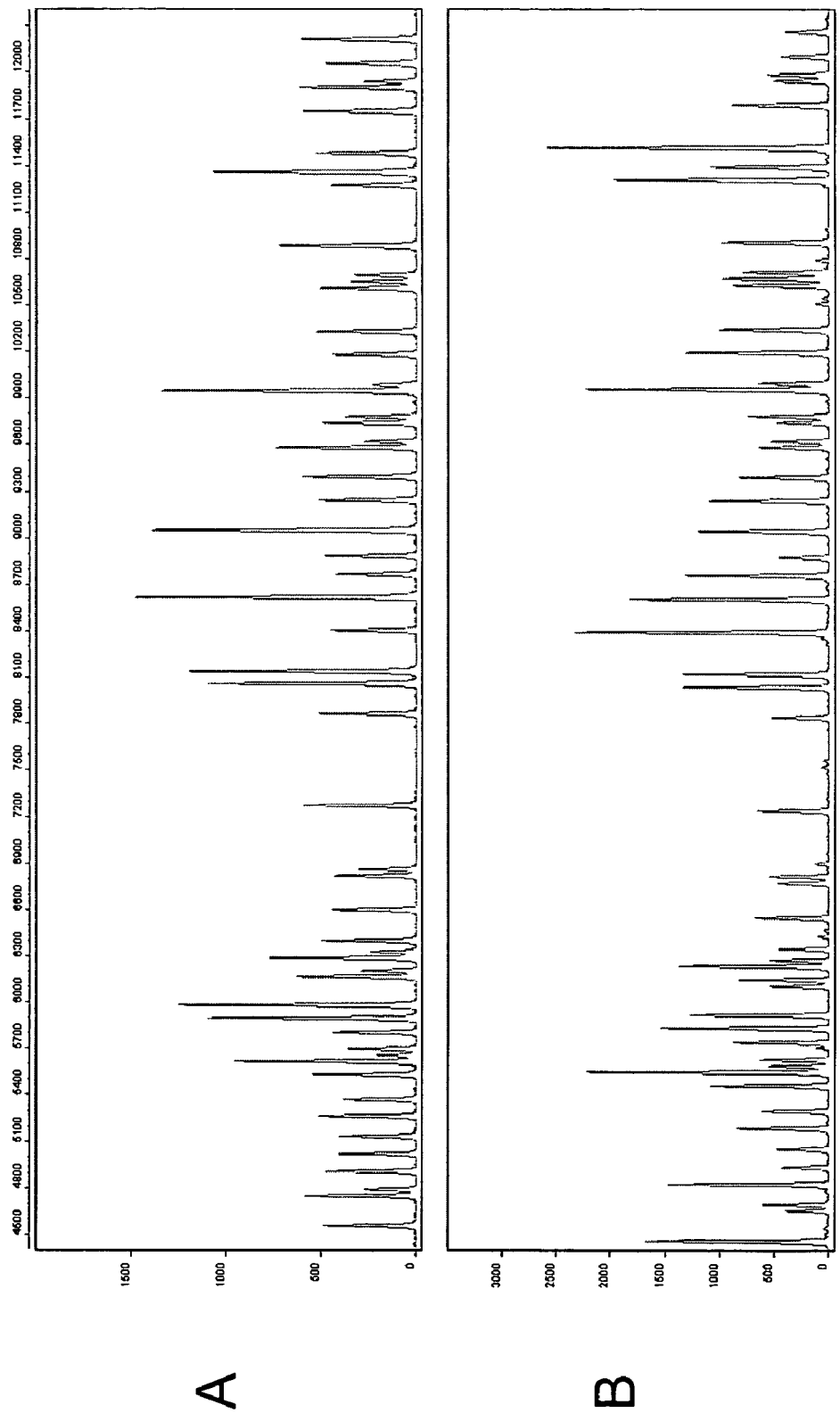
FIGS. 22A and B are spectral profiles that show the data from a sequence analysis of an M13mp18 DNA template using an unlabeled primer and a fluorescent dye-labeled 2'-terminator nucleotide.

Data was analyzed with Applied Biosystems GeneScan 3.7 fragment analysis software. FIG. 22 shows the fragment pattern for T peaks 77 to 273 bases from primer FR686N. More specifically, comparison of the fragment pattern generated with G46E E678G CS5 DNA polymerase and TAMRA-uridine 2'-monophosphate 5'-triphosphate (panel B) to the fragment pattern generated with the control AmpliTaq DNA Polymerase, FS and TAMRA-ddTTP (panel A) revealed a similar pattern of peaks.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A composition comprising a nucleoside or a nucleotide comprising the formula:

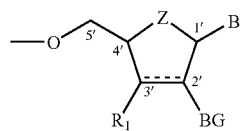

wherein $R_1$ is H, OH, a hydrophilic group, or a hydrophobic group;

B is at least one homocyclic ring, at least one heterocyclic ring, at least one aryl group, or combinations thereof;
BG is a blocking group which is a phosphate group —H$_2$PO$_4$
Z is O or CH$_2$; and
---- represents a single or double bond;
wherein the nucleoside or nucleotide is labeled; and,
further comprising
one or more nucleotide incorporating biocatalysts selected from the group consisting of: G46E E678G CS5 DNA polymerase, a G46E L329A E678G CS5 DNA polymerase, G46E E678G CS6 DNA polymerase, Δ ZO5R polymerase, E615G Taq DNA polymerase, *Thermus flavus* polymerase, TMA-25 polymerase, TMA-30 polymerase, Tth DNA polymerase, *Thermus* specie SPS-17 polymerase, E615G Taq polymerase, *Thermus* ZO5R polymerase, T7 DNA polymerase, Kornberg DNA polymerase I, Klenow DNA polymerase, Taq DNA polymerase, Micrococcal DNA polymerase, alpha DNA polymerase, reverse transcriptase, AMV reverse transcriptase, M-MuLV reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase, and ribonucleotide incorporating DNA polymerase,
wherein the nucleoside or nucleotide is non-extendible by said one or more nucleotide incorporating biocatalysts.

2. The composition of claim 1, wherein B comprises the formula:

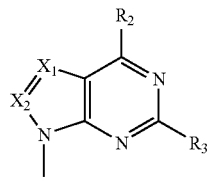

wherein
X$_1$ and X$_2$ are independently selected from CH and N;
R$_2$ is H, OH, or NR$_4$R$_5$;
R$_3$ is H, OH, or NR$_6$R$_7$;
R$_4$ and R$_5$ are independently selected from H, an alkyl group, an alkenyl group, an alkynyl group, a benzyl group, an aryl group, an aryloxy group, and combinations thereof; and,
R$_6$ and R$_7$ are independently selected from H, an alkyl group, an alkenyl group, an alkynyl group, a benzyl group, an aryl group, an aryloxy group, and combinations thereof.

3. The composition of claim 1, wherein B comprises the formula:

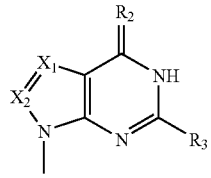

wherein
X$_1$ and X$_2$ are independently selected from CH and N;
R$_2$ is O or S;
R$_3$ is H, OH, or NR$_4$R$_5$; and, R$_4$ and R$_5$ are independently selected from H, an alkyl group, an alkenyl group, an alkynyl group, a benzyl group, an aryl group, an aryloxy group, and combinations thereof.

4. The composition of claim 1, wherein B comprises the formula:

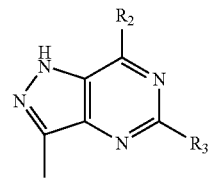

wherein
R$_2$ is H, OH, or NR$_4$R$_5$;
R$_3$ is H, OH, or NR$_6$R$_2$;
R$_4$ and R$_5$ are independently selected from H, an alkyl group, an alkenyl group, an alkynyl group, a benzyl group, an aryl group, an aryloxy group, and combinations thereof; and,
R$_6$ and R$_7$ are independently selected from H, an alkyl group, an alkenyl group, an alkynyl group, a benzyl group, an aryl group, an aryloxy group, and combinations thereof.

5. The composition of claim 1, wherein B comprises the formula:

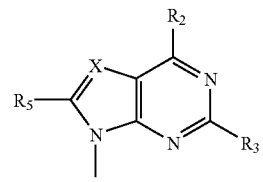

wherein
X is CH or N;
R$_2$ and R$_3$ are independently selected from H, OH, and NHR$_4$;
R$_4$ is H, an alkyl group, an alkenyl group, an alkynyl group, a benzyl group, an aryl group, an aryloxy group, or combinations thereof; and,
R$_5$ is OH, NH$_2$, SH, a halo group, an ether group, a thioether group, an alkyl group, an alkenyl group, an alkynyl group, an alkylamine group, an alkenylamine group, an alkynylamine group, or combinations thereof.

6. The composition of claim 1, wherein B comprises the formula:

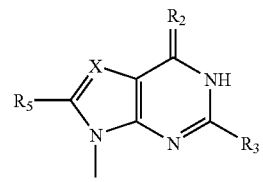

wherein X is CH or N;
R$_2$ is O or S;
R$_3$ is H, OH, or NHR$_4$;
R$_4$ is H, an alkyl group, an alkenyl group, an alkynyl group, a benzyl group, an aryl group, an aryloxy group, or combinations thereof; and, $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

7. The composition of claim 1, wherein B comprises the formula:

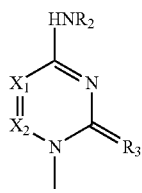

wherein $X_1$ and $X_2$ are independently selected from CH and N;

$R_2$ is H, an alkyl group, an alkenyl group, an alkynyl group, a benzyl group, an aryl group, an aryloxy group, or combinations thereof; and, $R_3$ is O or S.

8. The composition of claim 1, wherein B comprises the formula:

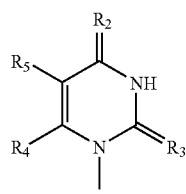

wherein $R_2$ and $R_3$ are independently selected from O and S; and, $R_4$ and $R_5$ are independently selected from H, $NH_2$, SH, OH, an alkyl group, an alkenyl group, an alkynyl group, a benzyl group, an aryl group, an aryloxy group, an alkoxy group, a halo group, and combinations thereof.

9. The composition of claim 1, wherein B comprises the formula:

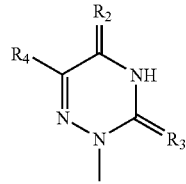

wherein $R_2$ and $R_3$ are independently selected from O and S; and, $R_4$ is H, $NH_2$, SH, OH, an alkyl group, an alkenyl group, an alkynyl group, a benzyl group, an aryl group, an aryloxy group, an alkoxy group, a halo group, or combinations thereof.

10. The composition of claim 1, wherein B comprises the formula

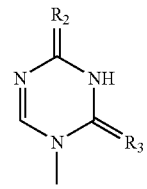

wherein $R_2$ and $R_3$ are independently selected from O and S.

11. The composition of claim 1, wherein B comprises the formula:

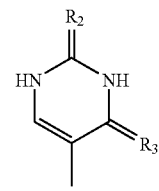

wherein $R_2$ and $R_3$ are independently selected from O and S.

12. The composition of claim 1, wherein B comprises the formula:

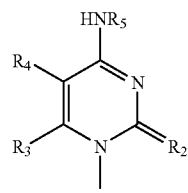

wherein $R_2$ is O or S;

$R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and, $R_5$ is an alkyl group, an alkoxy group, an alkenyl group, an alkenoxy group, an alkynyl group, an alkynoxy group, an aryl group, an aryloxy group, a benzyl group, a benzyloxy group, or combinations thereof.

13. The composition of claim 1, wherein B comprises or is attached to the label.

14. The composition of claim 1, wherein a sugar moiety of the nucleoside and/or nucleotide comprises or is attached to the label.

15. The composition of claim 1, wherein a linker comprises or attaches the label to the nucleoside and/or nucleotide.

16. The composition of claim 1, wherein at least one of the nucleotide incorporating biocatalysts is capable of extending a primer nucleic acid to produce an extended primer nucleic acid, incorporating the nucleotide at a terminal end of the extended primer nucleic acid.

17. The composition of claim 1, wherein the nucleotide comprises at least 1 phosphate group attached at the 5' position.

18. The composition of claim 1, wherein the label comprises a fluorescent dye, a weakly fluorescent label, a non-fluorescent label, a colorimetric label, a chemiluminescent label, a bioluminescent label, a radioisotope, an antibody, an antigen, biotin, a hapten, or an enzyme.

19. The composition of claim 18, wherein the label is a fluorescent dye selected from the group consisting of: a rhodamine dye, a fluorescein dye, a halofluorescein dye, a dichlororhodamine dye, an energy transfer dye, a Lucifer dye, Oregon Green, and a cyanine dye.

20. The composition of claim 19, wherein the fluorescent dye is selected from the group consisting of: JOE, VIC, TET, HEX, FAM, R6G, R110, TAMRA, and ROX.

21. The composition of claim 18, wherein the radioisotope is selected from the group consisting of: $^3$H, $^{14}$C, $^{22}$Na, $^{32}$P, $^{33}$P, $^{35}$S, $^{42}$K, $^{45}$Ca, $^{59}$Fe, $^{125}$I, and $^{203}$Hg.

22. The composition of claim 1, wherein the label comprises at least one mass-modifying group.

23. The composition of claim 22, wherein the mass-modifying group is selected from the group consisting of: deuterium, F, Cl, Br, I, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNY_2$, $CH_2CONY_2$, $(CH_2)_nOH$, $CH_2F$, $CHF_2$, $CF_3$, and a phosphorothioate group, wherein:

X is O, NH, NY, S, NHC(S), OCO(CH)$_n$COO, NHCO(CH$_2$)$_n$COO, OSO$_2$O, OCO(CH$_2$)$_n$, NHC(S)NH, OCO(CH$_2$)$_n$S, OCO(CH$_2$)S, NC$_4$O$_2$H$_2$S, OPO(O-alkyl), or OP(O-alkyl);

n is an integer from 1 to 20 inclusive; and,

Y is H, deuterium, an alkyl group, an alkoxy group, an aryl group, a polyoxymethylene group, a monoalkylated polyoxymethylene group, a polyethylene imine group, a polyamide group, a polyester group, an alkylated silyl group, a heterooligo, a polyaminoacid, a heterooligo/polyaminoacid group, or a polyethylene glycol group.

24. The composition of claim 1, further comprising one or more extendible nucleotides.

25. The composition of claim 24, wherein the extendible nucleotides comprise ribonucleotides and/or deoxyribonucleotides.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (19)..(19)
<223> OTHER INFORMATION: n is 2'-amino (ribo) C

<400> SEQUENCE: 1
cgccagggtt ttcccagtna                                              20
```